US009936977B2

(12) United States Patent
Hawkins et al.

(10) Patent No.: US 9,936,977 B2
(45) Date of Patent: Apr. 10, 2018

(54) REVISABLE ORTHOPEDIC ANCHOR AND METHODS OF USE

(71) Applicant: DePuy Synthes Products, Inc., Raynham, MA (US)

(72) Inventors: John Riley Hawkins, Cumberland, RI (US); Alexander Grinberg, Newton, MA (US); Michael Michielli, Medway, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 31 days.

(21) Appl. No.: 14/858,866

(22) Filed: Sep. 18, 2015

(65) Prior Publication Data

US 2016/0008033 A1 Jan. 14, 2016

Related U.S. Application Data

(63) Continuation of application No. 13/222,389, filed on Aug. 31, 2011, now Pat. No. 9,173,683.

(51) Int. Cl.
*A61F 2/44* (2006.01)
*A61B 17/70* (2006.01)
(Continued)

(52) U.S. Cl.
CPC ...... *A61B 17/7001* (2013.01); *A61B 17/0401* (2013.01); *A61B 17/7037* (2013.01);
(Continued)

(58) Field of Classification Search
CPC .................. A61F 2/44–2/447; A61F 2/4611; F16B 15/04
See application file for complete search history.

(56) References Cited

U.S. PATENT DOCUMENTS 2,238,463 A 4/1941 Dubilier
5,094,577 A 3/1992 Clark et al.
(Continued)

FOREIGN PATENT DOCUMENTS

WO 2010/028045 A1 3/2010
WO 2011/056990 A2 5/2011
WO 2011/098747 A2 8/2011

*Primary Examiner* — Jan Christopher Merene
*Assistant Examiner* — Steven Cotroneo
(74) *Attorney, Agent, or Firm* — Nutter McClennen & Fish LLP

(57) ABSTRACT

A revisable orthopedic anchor and method of use for removably securing an anchor in bone, such as compromised or degenerated bone, is described herein. In one embodiment, the anchor makes use of dual probes and vector divergence of the distal tips of the probes to achieve superior bone purchase and pull-out resistance. In such an embodiment, the probes can be inserted one at a time into a hole formed in, for example, the pedicle bone. After the probes are inserted and joined at the proximal end, they have a greater pull-out resistance than a threaded anchor. Removing the anchor involves separating the proximal heads and reversing the implantation process. As a result of the unique bone anchor design disclosed herein, the devices and methods of the present invention allow for less complicated implantation and removal of orthopedic anchors, all while providing enhanced bone purchase when implanted in a patient.

20 Claims, 25 Drawing Sheets

(51) Int. Cl.
| | |
|---|---|
| *A61B 17/04* | (2006.01) |
| *A61F 2/46* | (2006.01) |
| *A61B 17/86* | (2006.01) |
| *A61B 17/84* | (2006.01) |
| *A61F 2/30* | (2006.01) |
| *A61F 2/28* | (2006.01) |

(52) U.S. Cl.
CPC ...... *A61B 17/7049* (2013.01); *A61B 17/7076* (2013.01); *A61F 2/447* (2013.01); *A61F 2/4611* (2013.01); *A61B 17/844* (2013.01); *A61B 17/8685* (2013.01); *A61B 2017/0414* (2013.01); *A61B 2017/8655* (2013.01); *A61F 2/30965* (2013.01); *A61F 2002/2817* (2013.01); *A61F 2002/2835* (2013.01); *A61F 2002/30509* (2013.01); *A61F 2002/30607* (2013.01); *A61F 2002/30616* (2013.01); *A61F 2002/30779* (2013.01); *A61F 2002/30787* (2013.01); *A61F 2002/30828* (2013.01); *A61F 2002/30843* (2013.01); *A61F 2002/4475* (2013.01); *A61F 2310/00023* (2013.01)

(56) References Cited

U.S. PATENT DOCUMENTS

| | | | |
|---|---|---|---|
| 5,846,041 A | 12/1998 | Bevan et al. | |
| 5,935,169 A | 8/1999 | Chan | |
| 5,984,681 A * | 11/1999 | Huang | A61C 8/001 433/173 |
| 6,224,631 B1 | 5/2001 | Kohrs | |
| 6,485,517 B1 * | 11/2002 | Michelson | A61B 17/7059 623/17.11 |
| 6,533,791 B1 | 3/2003 | Betz et al. | |
| 6,736,847 B2 | 5/2004 | Seyr et al. | |
| 7,527,638 B2 | 5/2009 | Anderson et al. | |
| 7,682,377 B2 | 3/2010 | Konieczynski et al. | |
| 7,744,649 B2 | 6/2010 | Moore | |
| 7,875,056 B2 | 1/2011 | Jervis et al. | |
| 8,007,534 B2 | 8/2011 | Michelson | |
| 8,267,966 B2 | 9/2012 | McCormack et al. | |
| 8,333,591 B2 * | 12/2012 | Zhao | A61C 8/001 433/174 |
| 8,343,189 B2 | 1/2013 | Assell et al. | |
| 8,685,104 B2 * | 4/2014 | Lee | A61F 2/447 623/17.11 |
| 9,173,683 B2 | 11/2015 | Hawkins et al. | |
| 2002/0099376 A1 * | 7/2002 | Michelson | A61F 2/4611 606/86 A |
| 2002/0161443 A1 * | 10/2002 | Michelson | A61F 2/4455 623/17.11 |
| 2003/0078668 A1 * | 4/2003 | Michelson | A61B 17/7059 623/17.16 |
| 2005/0055027 A1 * | 3/2005 | Yeung | A61B 17/0401 606/75 |
| 2006/0264939 A1 | 11/2006 | Zucherman et al. | |
| 2009/0005870 A1 | 1/2009 | Hawkins et al. | |
| 2009/0055733 A1 | 2/2009 | Graeber | |
| 2009/0105832 A1 * | 4/2009 | Allain | A61B 17/0642 623/17.16 |
| 2010/0057141 A1 | 3/2010 | Abdelgany et al. | |
| 2010/0063550 A1 | 3/2010 | Felix et al. | |
| 2010/0145397 A1 * | 6/2010 | Overes | A61B 17/68 606/319 |
| 2010/0185289 A1 * | 7/2010 | Kirwan | A61F 2/4455 623/17.11 |
| 2011/0230920 A1 * | 9/2011 | Gorek | A61B 17/7001 606/305 |
| 2012/0099946 A1 * | 4/2012 | Hung | F16B 15/04 411/509 |
| 2012/0265259 A1 * | 10/2012 | LaPosta | A61B 17/8894 606/86 A |
| 2013/0053891 A1 | 2/2013 | Hawkins et al. | |

* cited by examiner

REVISABLE ORTHOPEDIC ANCHOR AND METHODS OF USE

CROSS-REFERENCE TO RELATED APPLICATIONS

The present application is a continuation of U.S. application Ser. No. 13/222,389 filed on Aug. 31, 2011 and entitled "REVISABLE ORTHOPEDIC ANCHOR AND METHODS OF USE," the entire content of which is hereby incorporated herein by reference.

FIELD

This invention is related to bone anchors for use in orthopedic surgery and, in particular, to devices and methods for implanting an anchor in bone such that the anchor provides enhanced bone purchase during use as well as easy removal.

BACKGROUND

Bone in human and other mammal bodies is generally classified into two types, cortical bone, also known as compact bone, and trabecular bone, also known as cancellous or spongy bone. Cortical bone is much denser than trabecular bone with a porosity ranging between 5% and 10%. Cortical bone is found primarily in the shaft of long bones and forms the outer shell around trabecular bone at the end of joints and the vertebrae.

In the vertebrae, each bone is generally heart shaped, with spinous, inferior and superior processes joined to the vertebral body via opposing pedicles. To stabilize or fix deformities in the spine, implantable medical devices, known as spinal fixation devices, can be employed between adjacent vertebrae. These devices can be attached to the vertebrae using screws inserted through the pedicles (i.e., using "pedicle screws") and other osseous structures such as the lamina and facet joints.

The outer shell of the pedicles is formed of dense cortical bone, which surrounds spongier trabecular bone. As mentioned above, trabecular bone is normally less dense than cortical bone. Degenerative conditions, which can result from diseases such as osteoporosis or injury, can cause the trabecular bone to weaken or degrade even further.

As a result of the lower density of the trabecular or compromised bone, screws of all sizes can loosen or shift position after implantation. Prior art attempts to secure bone screws in the pedicles include features to prevent loosening of the screws. These features can include deflectable wings that push outwardly against the bone, or toggle-bolt-like fittings that rotate once inside the cortical bone shell to prevent removal therefrom. Other prior art systems make use of cement or other binding agent to secure the bone screw inside of the pedicle.

These prior art solutions, however, are not without potential drawbacks. For example, prior art implementations are designed to provide permanent fixation of the bone screw within the pedicle or other bone. Accordingly, removal of these components requires a complicated and oftentimes invasive procedure. In addition, some prior art solutions utilize traditional threaded screws that require pre-implantation operations to correctly drill and tap a hole through the bone.

Finally, in certain situations it can be desirable to utilize radiolucent materials to avoid interference with medical imaging technologies. Prior art implementations, however, often utilize metal bone screws that are substantially radiopaque. This can be because radiolucent materials (e.g., any of various polymer-based materials) are often not suitable for creating fine features like threading on a screw.

Hence, there is a need in the art for a device and method for securing an anchor in degenerated bone such that the anchor exhibits enhanced bone purchase while remaining easy to remove after use. Further, there is a need in the art to design these anchors such that they can be formed from radiolucent materials to prevent interference with medical imaging technologies.

SUMMARY

To overcome the above and other drawbacks of conventional systems, the present invention provides a revisable orthopedic anchor and method of use for removably securing an anchor in degenerated bone. In one embodiment, the anchor makes use of dual probes and vector divergence of the distal tips of the probes to achieve superior bone purchase. In said embodiment, the probes can be inserted one at a time into a hole formed in, for example, the pedicle bone. After the probes are inserted and joined at the proximal end, they have a greater pull-out resistance than a threaded anchor. Removing the anchor involves separating the proximal heads and reversing the implantation process. As a result of the unique designs disclosed herein, the devices and methods of the present invention allow for less complicated implantation and removal of orthopedic anchors, all while providing enhanced bone purchase once implanted in a patient.

In one aspect of the invention, a bone anchor is provided that includes a first probe component in the form of an elongate member having a proximal head and a distal tip. The first probe component further includes a bone engaging edge having a plurality of barbs, an opposed edge, an external surface, and an opposed internal surface having a guide shoulder formed thereon. The bone anchor also includes a second probe component in the form of an elongate member having a proximal head and a distal tip. The second probe component similarly includes a bone engaging edge having a plurality of barbs, a mating edge having a profile complimentary to the guide shoulder and being configured to be seated along the guide shoulder, an external surface, and an opposed internal surface. Optionally, the mating edge of the second probe member is curved. The first and second probe components are configured to be assembled to form a bone anchor such that the barbed bone engaging edges of the first and second probe components are disposed opposite to one another, the mating edge of the second probe component is seated along the guide shoulder of the first probe component, and the distal tip of each probe component diverges away from a central longitudinal axis of the anchor. The first and second probe members can optionally be curved elongate members.

The above-described bone anchor can include a variety of further features or modifications. For example, in some embodiments, the external surfaces of the first probe component and the second probe component can be convex. When the probes are assembled to form a bone anchor, the resulting cross-sectional shape can better adapt to the non-circular anthropometrics of the pedicle or other bone.

In other embodiments, the internal surfaces of the first probe component and the second probe component can be substantially linear. Linear internal surfaces provide for easy and secure mating between the first and second probe components when assembled to form a bone anchor. In still other embodiments, alternative profiles can be used, including, for example, convex/concave shapes, interlocking ridges (i.e., tongue and groove surfaces), complementary diagonals, etc.

The bone anchor can further include a crimp head configured to retain the proximal heads of the first probe component and the second probe component in a fixed relationship with each other. Such a crimp head can prevent the two probe components from separating after implantation. As explained below, maintaining the proximal heads in a fixed relationship with each other can be important to provide the bone anchor with its superior resistance to removal.

In certain embodiments, the proximal head of the first probe component and the second probe component can include a recess formed therein configured to seat a spinal fixation element. The seat formed by the probe components, in combination with a crimp head that forces the spinal fixation element into the seat, can securely attach a vertebral body to a spinal fixation element.

In other embodiments, the bone anchor can include a polyaxial receiving head configured to retain the proximal heads of the first probe component and the second probe component in a fixed relationship with each other. In these embodiments, the polyaxial receiving head replaces the above-mentioned crimp head to both hold the probe components together at their proximal ends and to secure a spinal fixation element to the bone anchor.

In still other embodiments, each of the first probe component and the second probe component can include a rod section joined to the proximal head thereof. Each rod section can be joined to form a spinal fixation element that can, in turn, be attached to adjacent bone anchors. The bone anchor can also include a crimp head configured to retain the proximal heads and rod sections of the first probe component and the second probe component in a fixed relationship with each other.

In certain embodiments, the bone anchor can include an implant configured to fuse two vertebral bodies together. The implant can include at least one lumen formed therein and configured to receive the first probe component and the second probe component.

In some embodiments, the implant can include a set screw configured to engage a threaded lumen formed in the implant to secure the first probe component and the second probe component in relation to each other and the implant.

The first and second probe components, and associated rod sections, if any, can be formed from a variety of materials. For example, the probe components and rod sections can be formed from any of titanium, a titanium alloy, polyether ether ketone (PEEK), and reinforced PEEK. The crimp head, polyaxial receiving head, and implant can each be formed from similar biocompatible materials.

In some embodiments, the first probe component and the second probe component are formed from a radiolucent material. Forming the probe components from radiolucent materials prevents the implanted anchor from interfering with medical imaging technologies (e.g., X-rays, etc.).

In another aspect of the invention, an implantable bone anchor is provided including an elongate member having a proximal head with a fixation element receiving seat and dual divergent distal tips. The bone anchor further includes opposed bone engaging edges having a plurality of barbs formed thereon. The bone anchor can be formed of separate matable probe components and each probe component has one of the divergent distal tips.

In some embodiments, each probe component is curved along its length from the proximal head to the divergent distal tip. This curve, combined with the dual divergent tips, results in an anchor that is wider at its distal end than at its proximal end. This configuration allows the anchor to resist being pulled out of the bone.

In some other embodiments, each probe component is mated to the other along at least a portion of an internal surface that is opposed to one of the bone engaging edges. As a result, the bone engaging edges of each probe component oppose each other and are configured to engage bone upon implantation. The bone engaging edges can include barbs or other protrusions configured to interface with a bone wall. In some embodiments, these barbs can be directionally oriented to allow travel in one direction (e.g., insertion), but oppose travel in an opposite direction (e.g., removal).

In a third aspect of the invention, a method of anchoring an implant to bone is provided comprising the steps of inserting a first probe member into a cavity formed in bone, where the first probe member is a curved, elongate member having a distal tip and a proximal head. The method further includes the step of inserting a second probe member into the cavity adjacent to the first probe member where the second probe member is a curved, elongate member having a distal tip and a proximal head, and where the first and second probe members mate to one another such that the heads of the first and second probe members are aligned and the distal tips of the first and second probe members diverge.

In some embodiments, the method step of inserting the second probe member includes sliding the second probe member along a guide shoulder formed in the first probe member to properly align the first probe member and the second probe member in the cavity.

In other embodiments, the method can further include the step of applying a crimp head to the proximal heads of the first probe member and the second probe member to retain the proximal heads in relation to each other.

In still other embodiments, the first probe member and the second probe member can each further include a rod section connected to the proximal head. The method can also include the step of aligning the rod sections of the first probe member and the second probe member to assemble a spinal fixation element. Still further, the method can include the step of applying a crimp head to retain the proximal heads and rod sections of the first probe member and the second probe member in relation to each other.

BRIEF DESCRIPTION OF THE DRAWINGS

The invention will be more fully understood from the following detailed description taken in conjunction with the accompanying drawings, in which.

DETAILED DESCRIPTION

Figure 1:
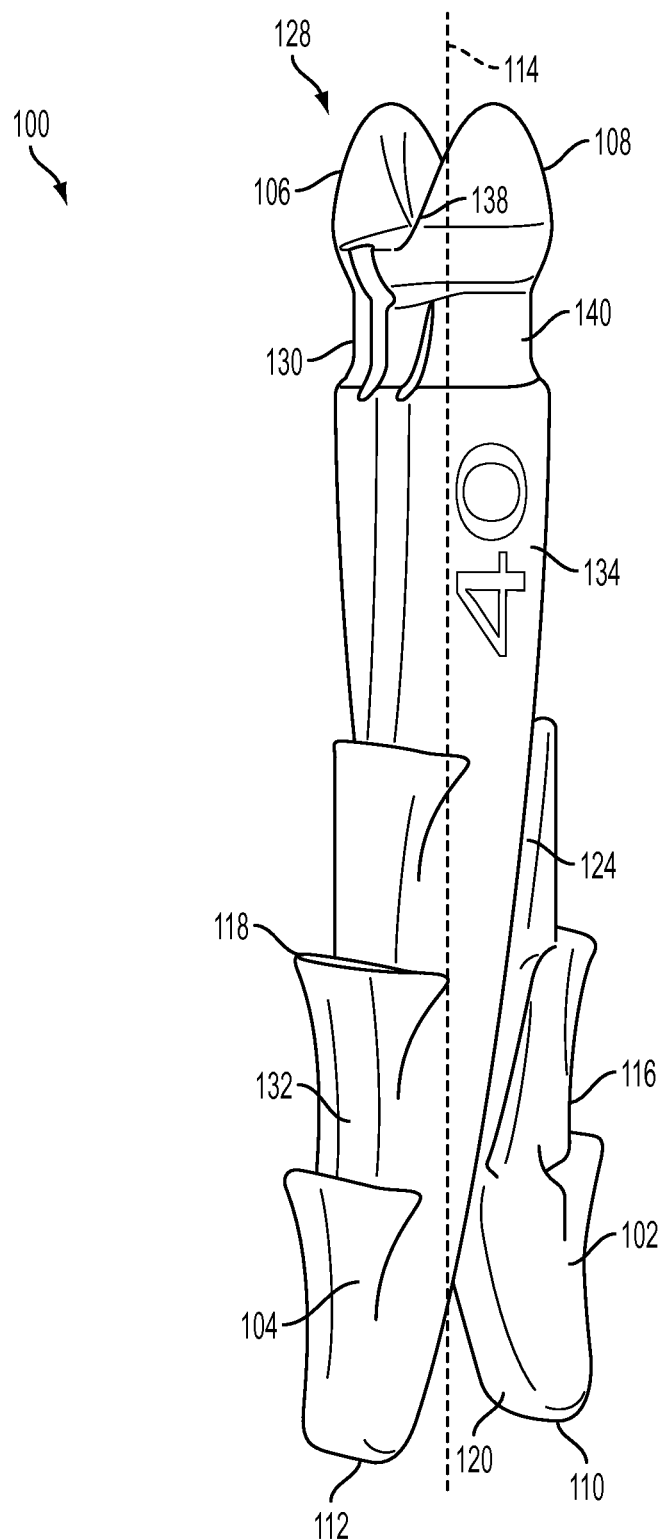
FIG. 1 is a perspective view of one embodiment of a bone anchor of the present invention comprising two probe components.

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In one aspect of the invention, a bone anchor is provided that includes two probe components configured to be assembled to form a complete bone anchor. Each probe component can be in the form of an elongate member having a proximal head and a distal tip. A first probe component can have a bone engaging edge, an opposed edge, an external surface, and an opposed internal surface having a guide shoulder formed thereon. A second probe component can have a bone engaging edge, a mating edge, an external surface, and an opposed internal surface. The mating edge of the second probe component can have a profile complementary to the guide shoulder of the first probe component and be configured to be seated along the guide shoulder. While the first and second probe members are illustrated herein as curved, one skilled in the art will appreciate that they may be linear and non-curved. Similarly, the mating edge of the second probe component is illustrated herein as having a curved profile, but it may alternatively be linear.

In use, the distal tips of the first and second probe components can be inserted sequentially into a small hole formed in, for example, a pedicle bone. Once inserted into the pedicle bone, the proximal heads of the first and second probe components can be joined together such that bone engaging edges of the first and second probe components are disposed opposite to one another, the mating edge of the second probe component can be seated along the guide shoulder of the first probe component, and the distal tips of the first and second probe components can diverge away from a central longitudinal axis of the bone anchor. The divergent distal tips of the bone anchor can allow the curved bone engaging surfaces to interface with, for example, the more dense cortical bone that forms the outer shell of the pedicle, thereby providing greater pull-out resistance than a traditional bone screw.

FIGS. 1, 1A, 2, and 2A illustrate a bone anchor 100 of the present invention comprising a first probe component 102 and a second probe component 104. The probe components 102, 104 are separate and designed to be mated together, for example, in the orientation shown in FIG. 1. In such an orientation, the proximal head 106 of the first probe component 102 and the proximal head 108 of the second probe component 104 are aligned while the distal tip 110 of the first probe component 102 and the distal tip 112 of the second probe component 104 diverge away from a central longitudinal axis 114 of the bone anchor.

Figure 1A:
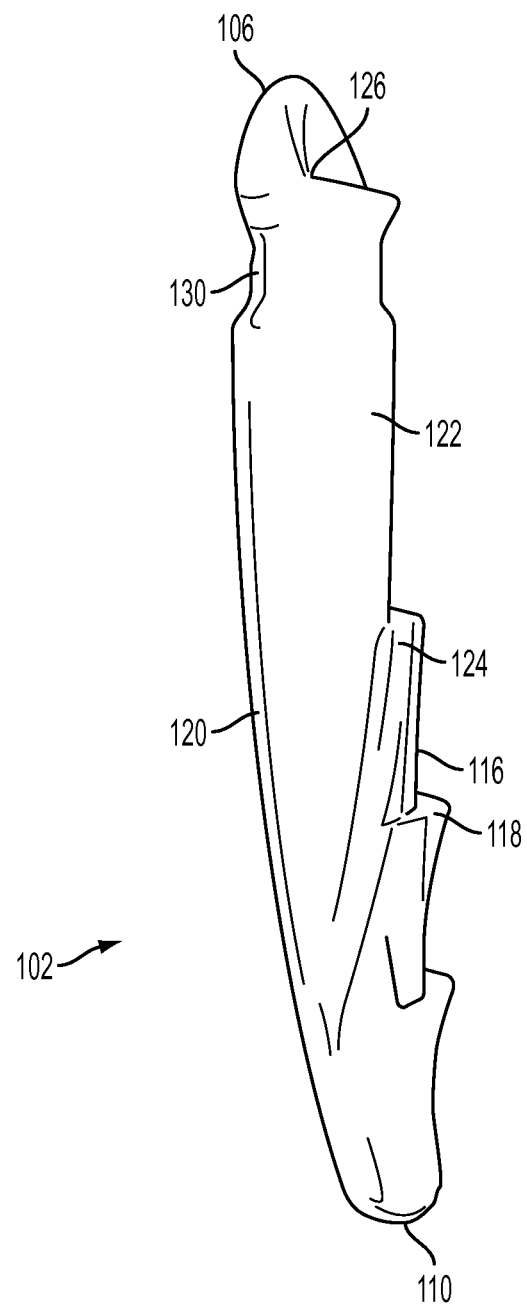
FIG. 1A is a perspective view of the first probe component of the bone anchor in FIG. 1.

The first probe component, shown in isolation in FIG. 1A, can include a bone engaging edge 116 having a plurality of barbs 118 formed thereon. Barbs 118 can be formed in a variety of shapes but, in an exemplary embodiment, the barbs can be formed with a one-way directional slant. The directional slant of the barbs allows advancement of the probe component into bone, but resists its removal. The first probe component can also include an opposed edge 120, which can have a smooth curved profile. One skilled in the art will appreciate that the barbs may additionally include, or they may be formed from, teeth, porous bone in-growth surfaces, and micro- or nano-features.

The first probe component can also include an internal surface 122 configured to interface with a portion of the second probe component 104. The internal surface 122 can be substantially linear to provide a planar surface to interface with the second probe component 104. The internal surface 122 can also include a guide shoulder 124 formed thereon that is also configured to interface with a portion of the second probe component 104. The guide shoulder 124 can be formed in a variety of shapes depending on the desired geometry of the bone anchor. In an exemplary embodiment, the guide shoulder 124 forms a diagonally extending curve across the internal surface 122 of the first probe component 102. In such a configuration, the guide shoulder 124 can gradually urge the distal tip 112 of the second probe component 104 to diverge from the distal tip 110 of the first probe component 102 as the second probe component is advanced down the length of the first probe component along the internal surface 122. Although not illustrated, the internal surface 122 may alternatively include one or more features formed thereon that are configured to mate with complementary features of the internal surface 206 of the second probe component 104.

Figure 2:
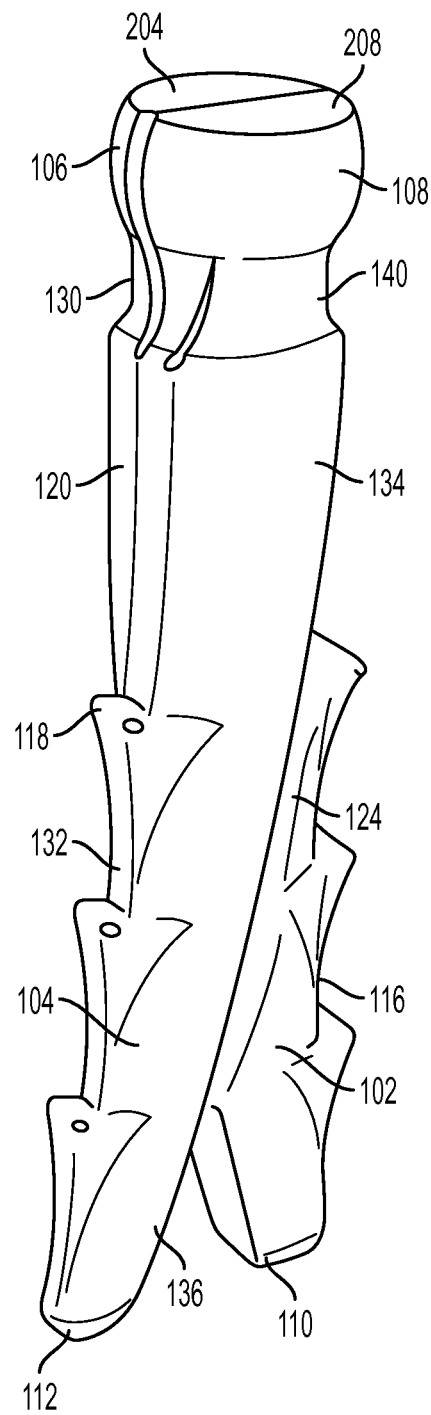
FIG. 2 is a perspective view of another embodiment of a bone anchor of the present invention having a flat top surface on its proximal end.
Figure 2A:
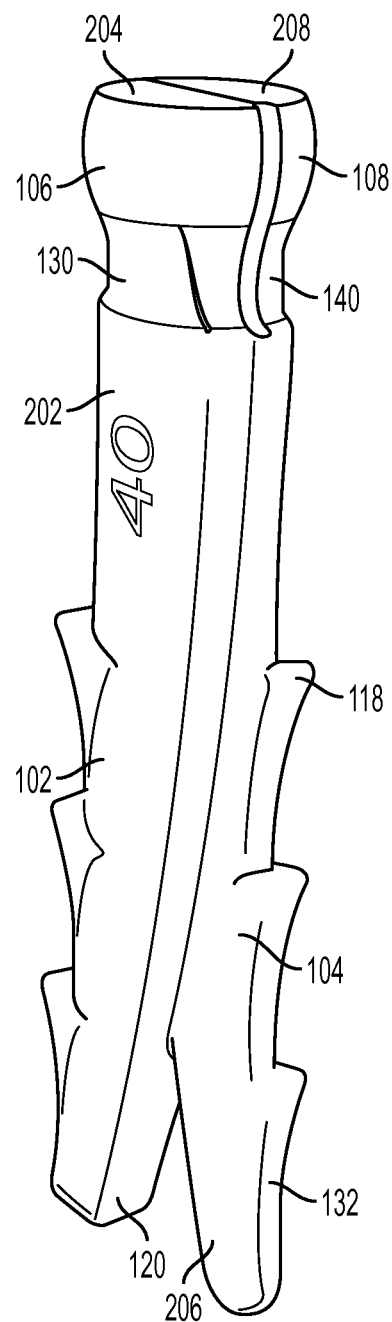
FIG. 2A is an alternate perspective view of the bone anchor in FIG. 2.

The first probe component 102 can further include an external surface 202, as shown in FIG. 2A. The external surface 202 can have a variety of profiles according to the geometry of the intended implantation site. In an exemplary embodiment, external surface 202 has a convex profile to adapt to the non-circular geometry of the pedicle bone, as discussed below.

Referring back to FIG. 1A, the first probe component 102 can include a proximal head 106 at its proximal end. Proximal head 106 can be formed in a variety of shapes and sizes according to the requirements of any receiving heads or other accessories to be attached to the bone anchor. In one embodiment, proximal head 106 can include a recess 126 formed therein and configured to form a fixation element receiving seat 128 (shown in FIG. 1) when combined with a complementary recess formed in the proximal head 108 of second probe component 104.

In other embodiments, proximal heads 106, 108 of the first and second probe components 102, 104 can have alternate geometries. For example, and as illustrated in FIGS. 2 and 2A, proximal heads 106, 108 can each include a flat surface 204, 208, or any other type of surface configured to interface with a receiving head assembly. Proximal heads 106, 108 of first and second probe components can also have a bulb-shape on their outer surfaces to allow polyaxial movement of attached receiving head assemblies having a socket-shaped cavity to receive the proximal heads 106, 108.

FIGS. 1 and 1A also illustrate a receiving head attachment portion 130 that can be included in the first probe component 102. Receiving head attachment portion 130 can be located distally from the proximal head 106 and can be configured to receive a mating feature from a receiving head or other accessory. In an exemplary embodiment, receiving head attachment portion 130 can be a narrowed section of the first probe component 102.

FIGS. 1, 2, and 2A also illustrate an exemplary embodiment of the second probe component 104. The second probe component 104 can have several features in common with the first probe component 102. These can include a bone engaging surface 132 having a plurality of barbs 118 formed thereon and an external surface 134 that can have a similar profile to the external surface 202 of first probe component 102 (e.g., a convex surface profile). As shown in FIG. 2A, the second probe component 104 can include an internal surface 206 opposed from external surface 134. The internal surface 206 can have a substantially linear surface profile in order to interface with the substantially linear internal surface 122 of the first probe component 102. Alternatively, however, and as noted above, the internal surface 206 can have features (not shown) that are configured to mate with complementary features (also not shown) of the internal surface 122.

Referring back to FIGS. 1 and 2, the second probe component 104 can include a mating edge 136 opposed from the bone engaging edge 132. The mating edge 136 can have a profile complementary to the profile of the guide shoulder 124. In an exemplary embodiment, the mating edge 136 has a curved profile matching the curve of guide shoulder 124. The complementary profiles allow the mating edge 136 to slide along the guide shoulder 124 as the second probe component 104 is implanted adjacent to the first probe component 102.

The second probe component 104 can also include similar components at its proximal end as the first probe component 102. For example, the second probe component can include a proximal head 108 configured to interface with a variety of spinal fixation components. Proximal head 108 can include, for example, a recess 138 formed therein that, in combination with recess 126 of the first probe component 102, can form a fixation element receiving seat 128. Alternatively, proximal head 108 can include a flat surface 208, as shown in FIG. 2. The second probe component 104 can also include a receiving head attachment portion 140 similar to the receiving head attachment portion 130 of the first probe component 102.

The first and second probe components can be formed from a variety of biocompatible materials suitable for implantation in a patient. These materials include, for example, metals such as titanium and titanium alloys, as well as polymers such as polyether ether ketone (PEEK) and reinforced PEEK. The design of the bone anchor of the present invention can be particularly well suited to the use of polymer-based materials. This is in contrast to traditional bone screw designs that have fine thread forms that cannot be reliably created with polymers. Another advantage of utilizing polymers like PEEK is the radiolucency of these materials. Unlike prior art metal bone screws, X-Ray and other medical imaging technologies can see through bone anchors formed from these radiolucent materials, providing medical professionals with a better image of the surrounding bone structure.

The first and second probe components can also be formed in a variety of sizes suited to the particular implantation site. In exemplary embodiments, the bone anchors are implanted in the pedicle bones of human vertebrae and are therefore sized accordingly. As discussed below, however, bone anchors of the present invention can be utilized in many different operations where tissue or implants need to be secured to bone. Variations on the size of the bone anchors to accommodate different implantation site geometries are considered within the scope of the invention.

As the foregoing description of the first and second probe components illustrates, an inventive aspect of the bone anchor disclosed herein is the ability to insert the first probe component 102 into a cavity formed in a bone, then insert the second probe component 104 and utilize the first probe component to aid in positioning the second probe component. This can be accomplished, for example, through the interaction of the guide shoulder 124 of the first probe component 102 and the mating edge 136 of the second probe component. After both probe components are implanted in the bone cavity, the proximal heads of the first and second probe components can be secured together to lock the probe components in the orientation shown in FIGS. 1 and 2.

Figure 3:
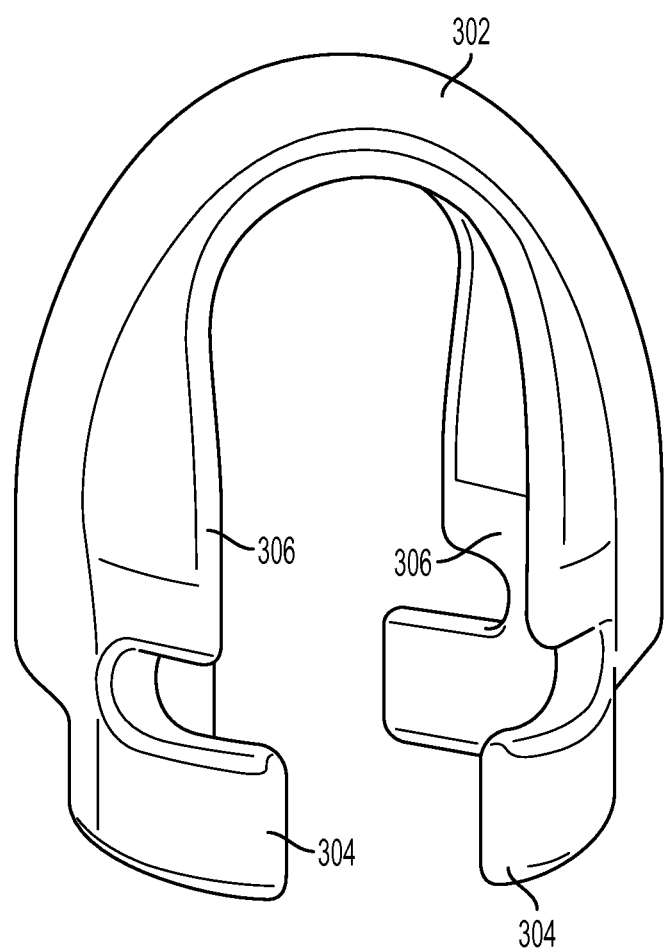
FIG. 3 is a perspective view of a crimp head configured to retain the proximal heads of the first and second probe components in a fixed relationship with each other and receive a spinal fixation element.

FIG. 3 illustrates an exemplary embodiment of a crimp head 300 that can be used to secure the proximal heads 106, 108 of the first and second probe components 102, 104 together. Crimp head 300 includes an arch portion 302 that extends between two sets of clamping arms 304. Crimp head 300 can further include recesses 306 configured to receive the bulb-shaped proximal heads 106, 108 of the first and second probe components 102, 104.

Figure 4:
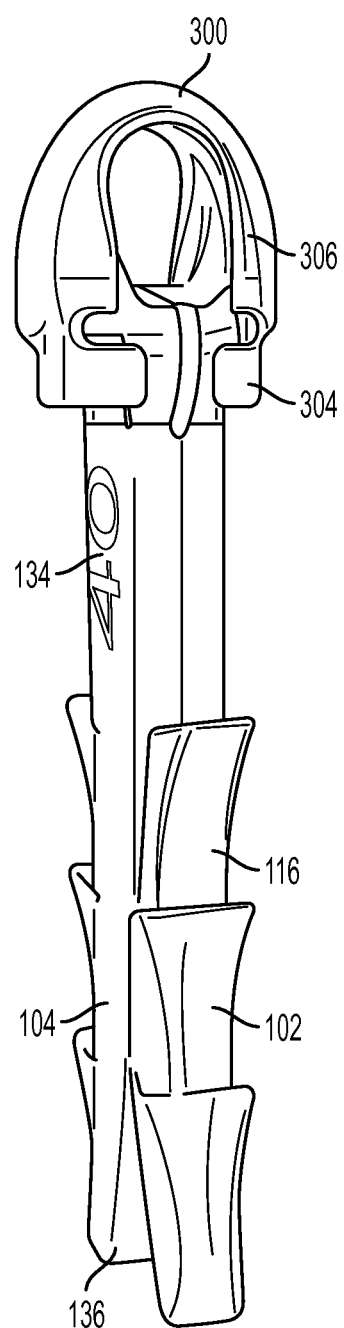
FIG. 4 is a perspective view of the bone anchor of FIG. 1, including the crimp head in FIG. 3.

FIG. 4 illustrates crimp head 300 in position over the first and second probe components shown in FIG. 1. In FIG. 4, crimp head 300 is shown in an un-compressed state in which there is a small amount of clearance between the clamping arms 304 and the receiving head attachment portion 130. There is also a small amount of clearance between the recesses 306 and the proximal heads 106, 108 of the first and second probe components 102, 104. This is done so that crimp head 300 can be placed over the top of the proximal head 106, 108 of first and second probe components 102, 104 without encountering resistance. To secure the crimp head 300 (and thereby secure the proximal heads 106, 108 in a fixed relationship with each other) a crimping tool (not shown) or other device suitable to provide compressive force to the clamping arms 304 can be used to position the clamping arms securely on the receiving head attachment portion 130, 140 of the first and second probe components.

FIG. 4 also illustrates that the arch portion 302 of crimp head 300, in combination with fixation element receiving seat 128, forms a closed lumen that can be used to secure a spinal fixation element to the bone. As a result, the bone anchor and crimp head of the present invention can be used to anchor spinal fixation elements to the vertebrae in place of traditional bone screws. An exemplary prior art system of spinal fixation is disclosed in U.S. Pat. No. 7,527,638 to Anderson et al., which is hereby incorporated by reference in its entirety.

Crimp head 300 can be formed from any of the same biocompatible materials mentioned above with respect to the first and second probe components. However, consideration should be given to the ability of the material to hold its shape under stress once crimped in position. In an exemplary embodiment, the crimp head 300 can be formed from a malleable material, such as titanium or a titanium alloy, in order to both allow deformation into the desired shape and to provide the necessary rigidity after implantation.

Figure 5:
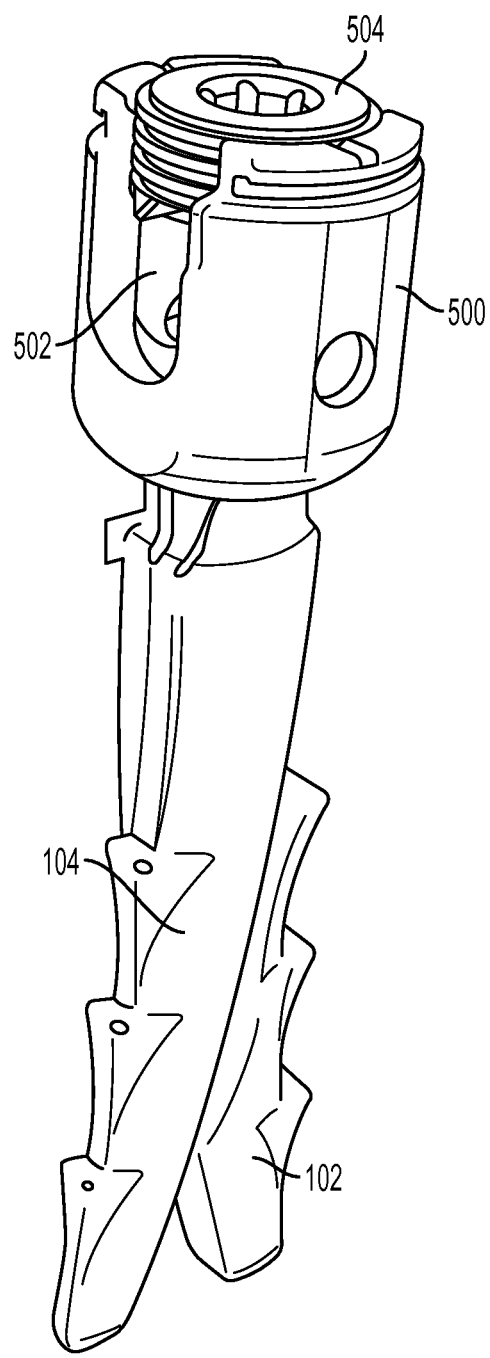
FIG. 5 is a perspective view of the bone anchor in FIG. 2, including a polyaxial receiving head configured to retain the proximal heads of the first and second probe components in a fixed relationship with each other and receive a spinal fixation element.
Figure 6:
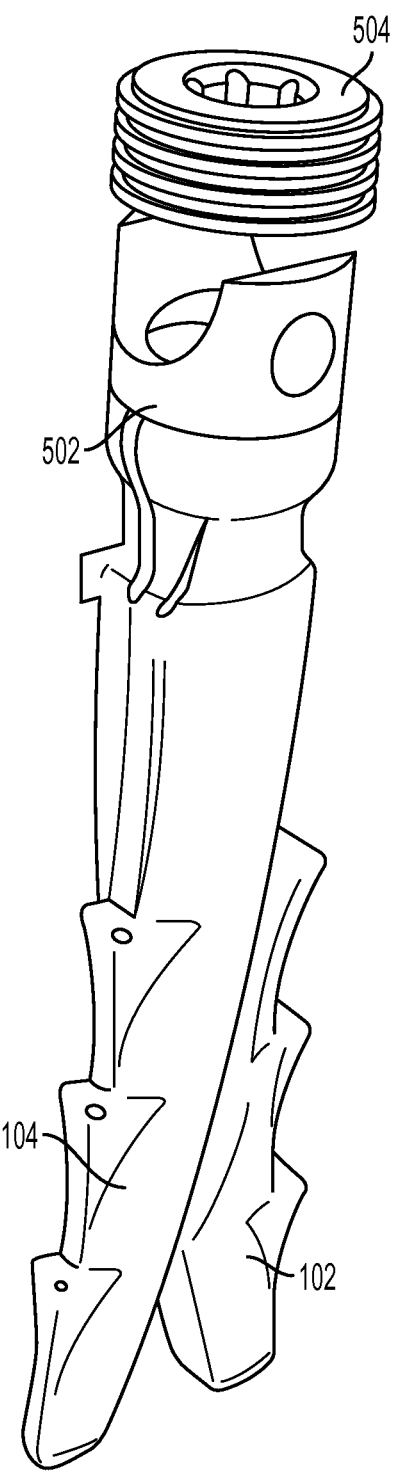
FIG. 6 is a perspective view of the bone anchor in FIG. 5 with the polyaxial receiving head hidden to reveal a spinal fixation element seat adapter and set screw.

The crimp head 300 is one embodiment of a receiving head assembly that can be attached to the bone anchor of the present invention. FIG. 5 illustrates another suitable receiving head assembly embodiment in the form of a polyaxial receiving head. Polyaxial receiving head 500 is similar to polyaxial receiving heads known in the prior art. U.S. Pat. No. 7,682,377 to Konieczynski et al., which is hereby incorporated by reference in its entirety, illustrates an exemplary prior art polyaxial receiving head. The polyaxial receiving head 500 can include a U-shaped transverse passage and a lumen for receiving the proximal heads 106, 108 of first and second probe components 102, 104. Polyaxial receiving head 500 can also include a spinal fixation element seat adapter 502 for use in embodiments having a flat surface 204, 208 on proximal heads 106, 108, as well as a set screw 504 that can be used to secure a spinal fixation element within the U-shaped transverse passage. FIG. 6 illustrates an alternate view of the bone anchor in FIG. 5 with the polyaxial receiving head hidden to better depict the spinal fixation element seat adapter 502 and set screw 504.

Figure 7:
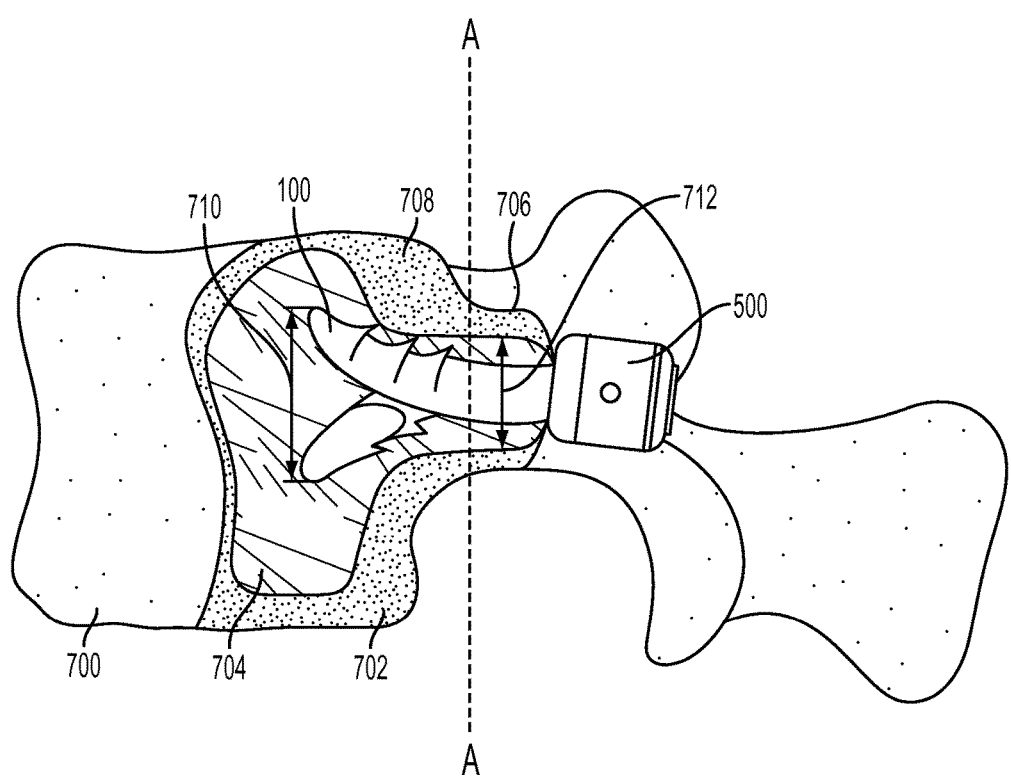
FIG. 7 is a cross-sectional view of the bone anchor in FIG. 5 implanted in a pedicle bone of a patient.

Having described exemplary components of the present invention, FIG. 7 depicts an exemplary bone anchor implanted within the pedicle bone of a patient's vertebrae in order to better illustrate each component's function. The partial cross section of the vertebrae 700 shows the outer layer of dense cortical bone 702 and the inner core of less dense trabecular bone 704. Implanted through the anterior portion of the pedicle bone 706 is bone anchor 100 including polyaxial receiving head 500.

Bone anchor 100 is able to achieve superior bone purchase in the pedicle 706 as a result of the curved shape of the first and second probe components 102, 104 and the associated divergent distal tips 110, 112. As FIG. 7 illustrates, the curved shape of the first and second probe components 102, 104 allows the bone engaging surfaces 116, 132 of the first and second probe components to interface with the stronger cortical bone forming the posterior rim 708 of the vertebral body. In addition, the combined probe width 710, which is measured as the distance between the divergent distal tips 110, 112 of the first and second probe components, is greater than the width 712 of the pedicle bone 706. As a result, the bone anchor 100 cannot be removed through the pedicle 706 so long as the polyaxial receiving head 500 retains the proximal ends 106, 108 of the first and second probe components 102, 104 in a fixed relationship with each other.

Figure 8:
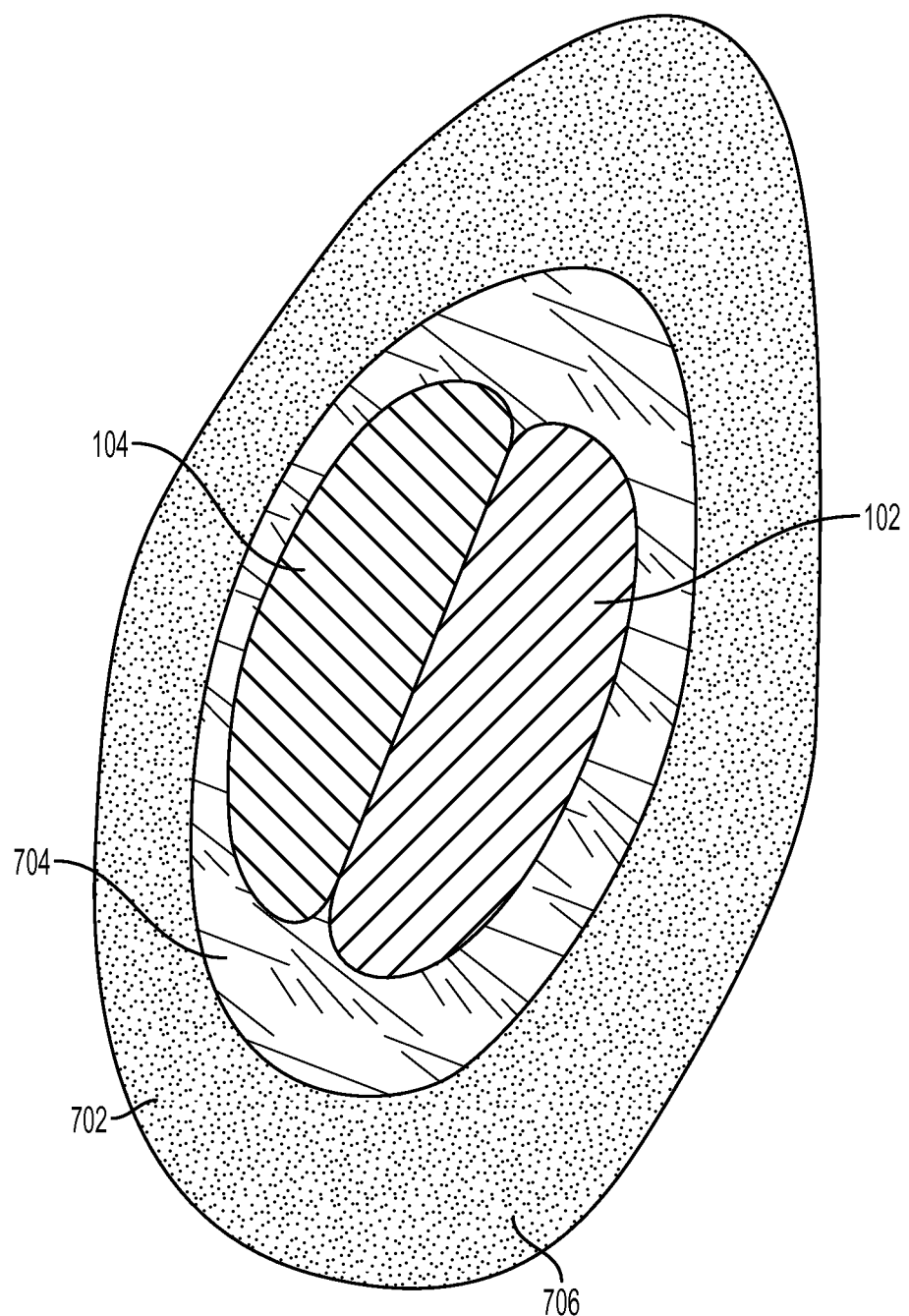
FIG. 8 is a cross-sectional view of the bone anchor in FIG. 7, taken along line A-A in FIG. 7, showing the complementary non-circular shape of the pedicle bone and probe components.

However, the width between divergent tips is not the only manner in which the bone anchor of the present invention utilizes anatomical geometry to its advantage. FIG. 8 illustrates a cross sectional view along the line A-A in FIG. 7. The figure illustrates that pedicle bone 706 (again, comprising a shell of cortical bone 702 and a core of trabecular bone 704) has a non-circular cross-sectional profile. Many known bone screws utilize circular cross sectional shapes, mostly due to limitations of processing the materials used to form the screws. Forming the first and second probe components 102, 104 of the present invention from polymer-based materials such as PEEK or reinforced PEEK allows for the creation of non-circular geometries that can better fill—and thus better anchor within—the pedicle bone 706 or other bone having non-circular geometry.

Figure 9:
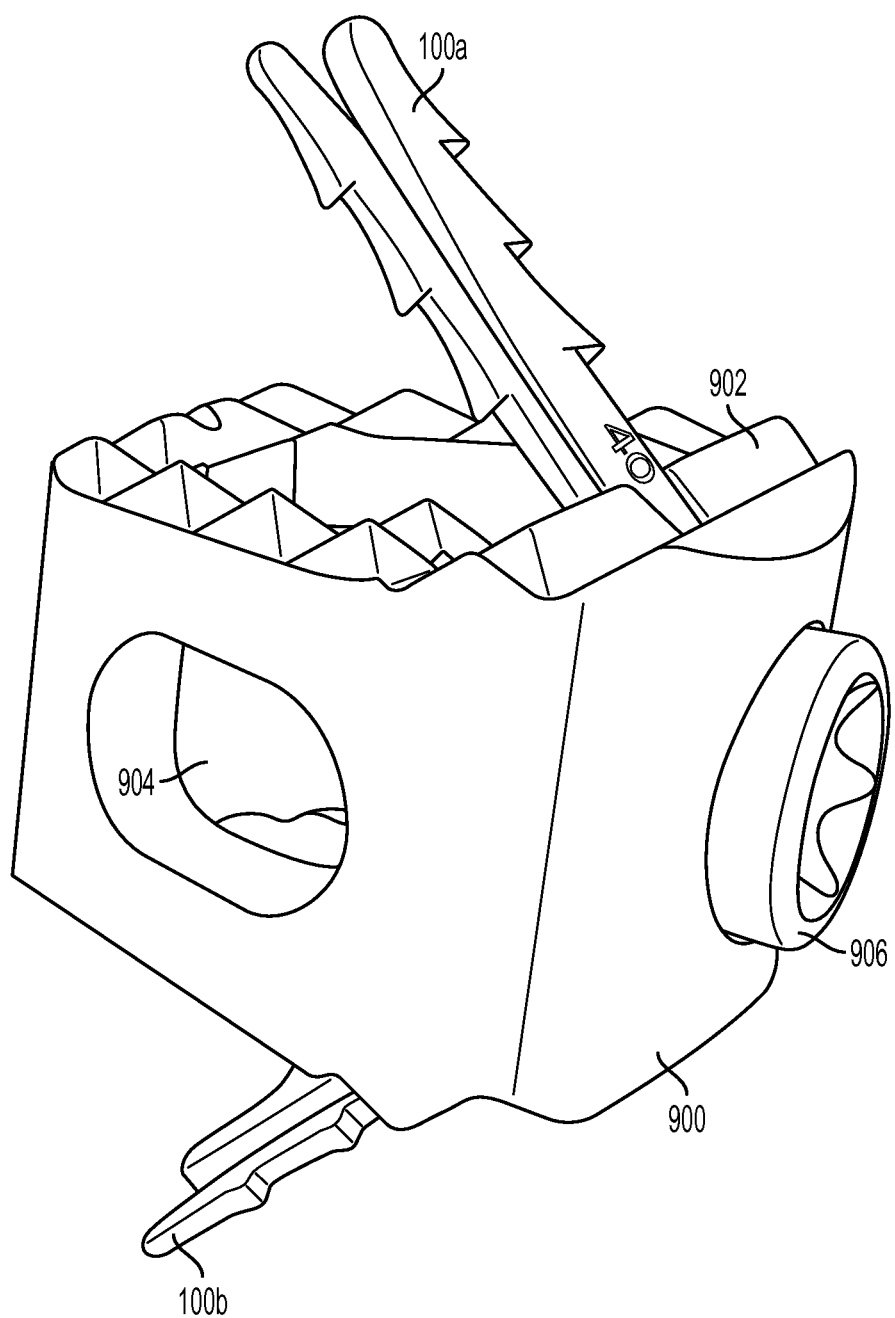
FIG. 9 is a perspective view of an embodiment of an implant of the present invention configured to fuse two vertebral bodies together including at least one bone anchor and a set screw.

In another embodiment, shown in FIG. 9, the bone anchor of the present invention includes an implant 900 configured to fuse two vertebral bodies together. The implant 900 can be used to replace a degenerated or injured intervertebral disc that exists between adjacent vertebrae. The implant 900 can include opposing textured surfaces 902, 904 configured to interface with a vertebral body. The implant 900 can further include an inner void 905 that can be filled with a biologic agent or other bone growth promoting material to stimulate natural bone growth that further anchors the implant 900 and fuses the vertebrae together.

Figure 10:
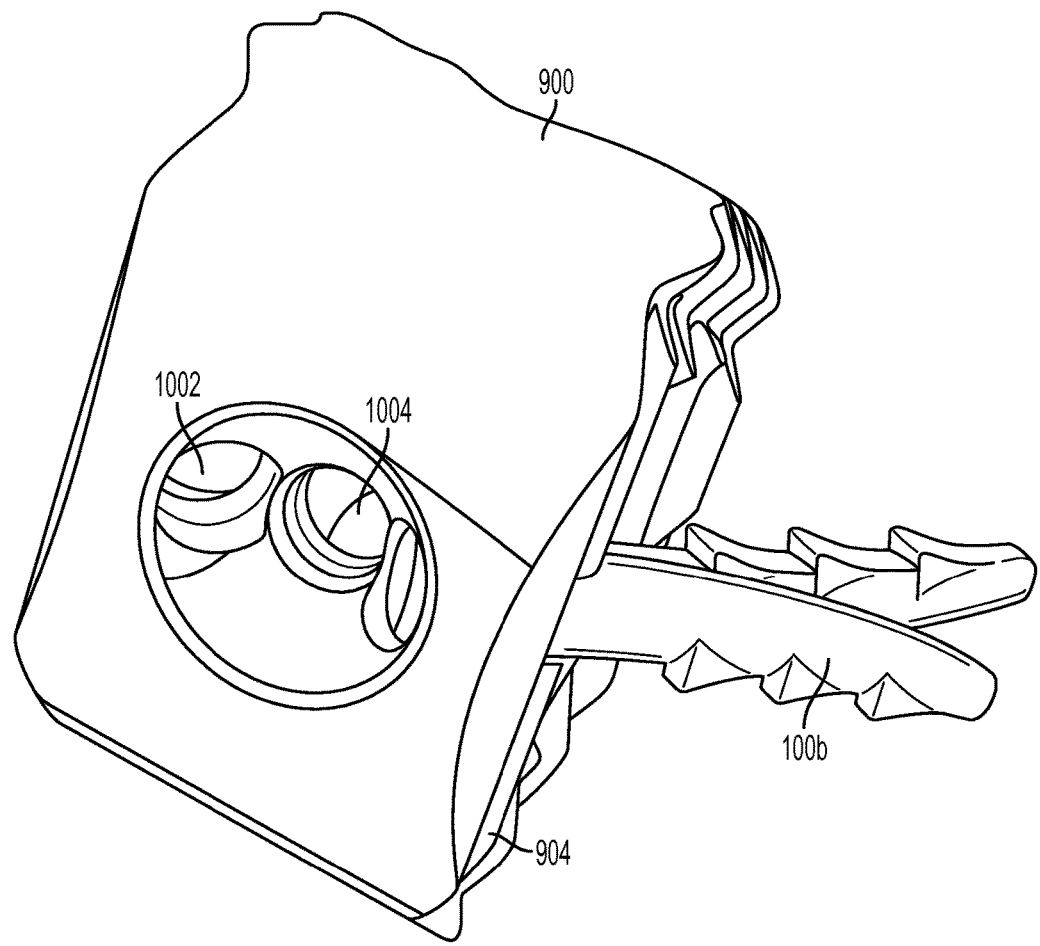
FIG. 10 is an alternate perspective view of the implant in FIG. 9 showing lumens configured to receive first and second probe components, as well as a threaded lumen configured to receive a set screw.

Implant 900 can be initially anchored to adjacent vertebral bodies using bone anchors 100a, 100b. As shown in FIG. 10, implant 900 can include one or more lumens 1002 configured to receive sets of first and second probe components that form bone anchors 100a and 100b, as discussed above. The lumens can be shaped to appropriately interface with the proximal heads 106, 108 of the first and second probe components, similar to the crimp head 300 and polyaxial receiving head 500 discussed above. Implant 900 can further include a threaded lumen 1004 configured to receive a set screw 906, which is shown in FIG. 9.

Figure 11:
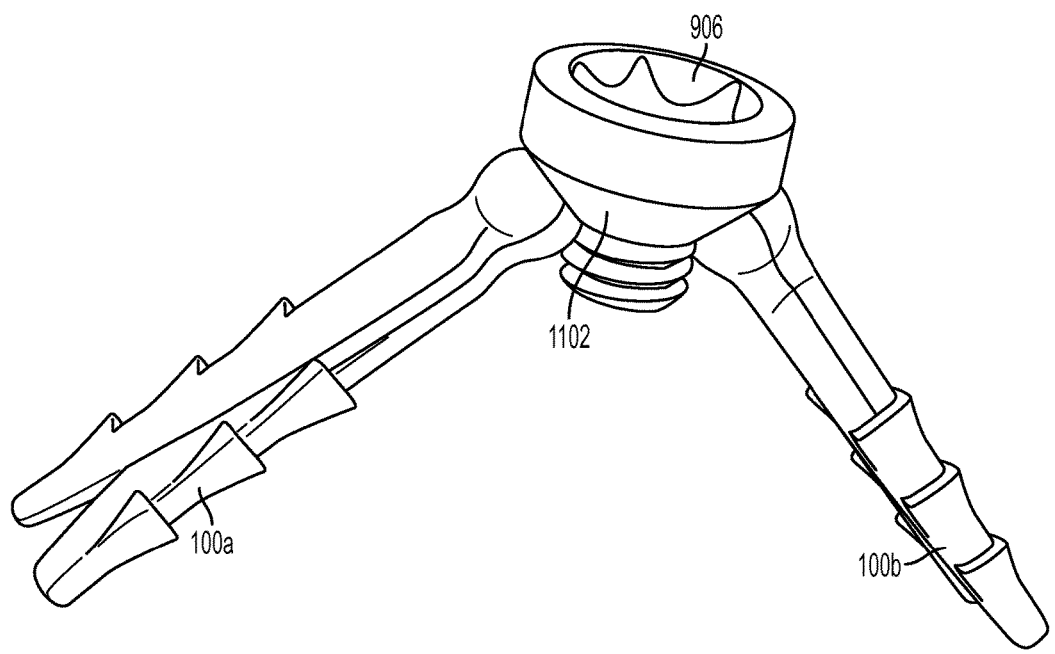
FIG. 11 is a perspective view of the implant in FIG. 9 with the implant body hidden to reveal the orientation and interaction between the bone anchors and the set screw.

As illustrated in FIG. 11, which shows the configuration of the set screw 906 and bone anchors 100a, 100b with the implant hidden, the set screw 906 can include an interface portion 1102 that interfaces with, for example, the flat surface 204, 208 of the first and second probe components of each bone anchor 100a, 100b. The set screw 906, in combination with the implant lumen 1002, retains the proximal heads 106, 108 of the first and second probe components 102, 104 in a fixed relationship with each other.

Figure 12:
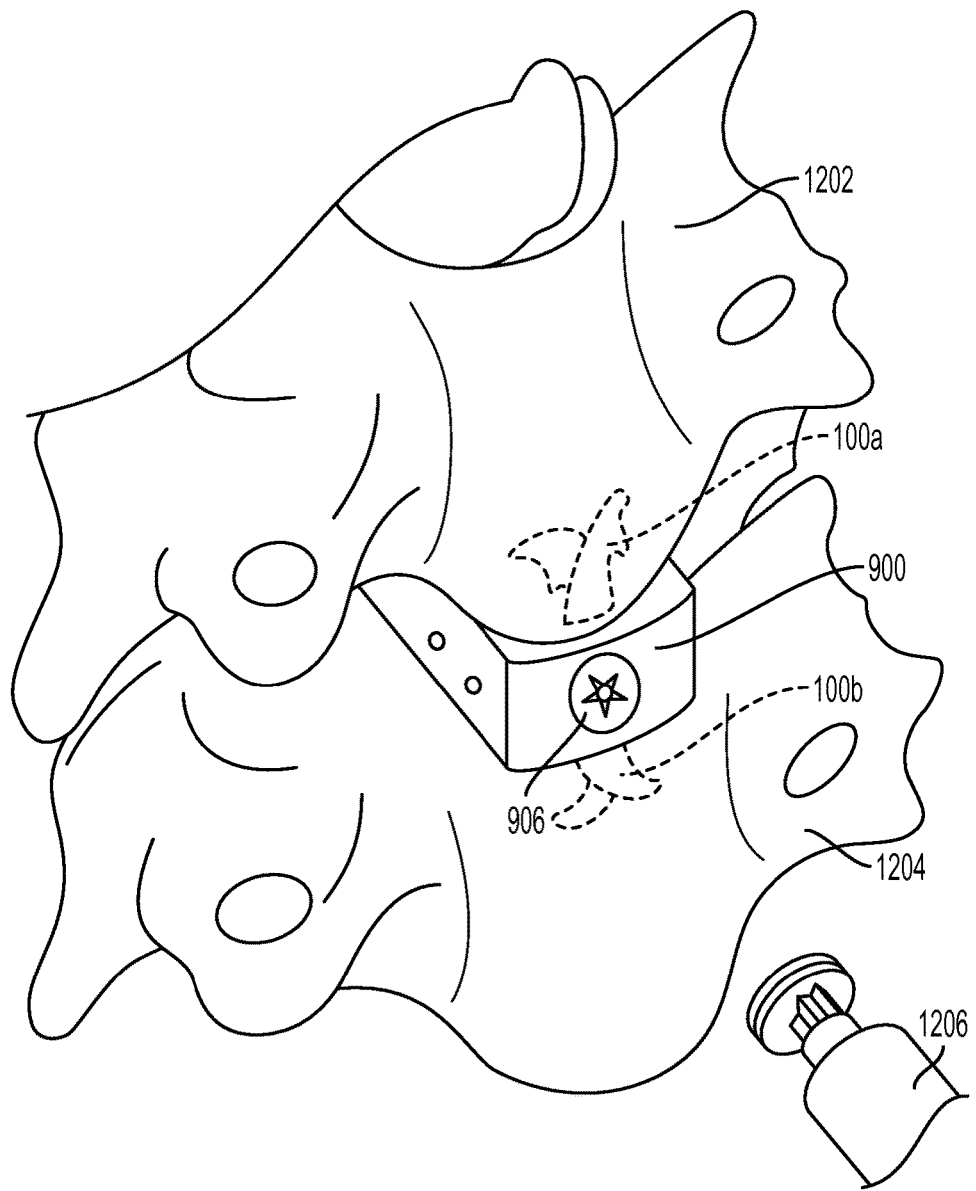
FIG. 12 is a perspective view of the implant in FIG. 9 in position between two vertebral bodies with implanted bone anchors shown in phantom.

FIG. 12 illustrates an exemplary embodiment of implant 900 in position between two vertebrae 1202, 1204. Bone anchors 100a, 100b are shown in phantom implanted within the vertebrae. The bone anchors illustrated in FIG. 12 are retained in position by the lumens formed in implant 900 and the set screw 906. Also shown in FIG. 12 is an exemplary applicator tool 1206 as known in the art for inserting and adjusting the set screw 906.

Still another embodiment of the invention provides a bone anchor as described above that further includes a rod section joined to each proximal head of the first and second probe components. In such an embodiment, when the first and second probe components are joined together, the associated rod sections can also be aligned to form a complete spinal fixation rod. This rod can be attached to additional bone anchors of the type described herein to create a complete spinal fixation assembly using fewer parts than was previously possible.

Figure 13:
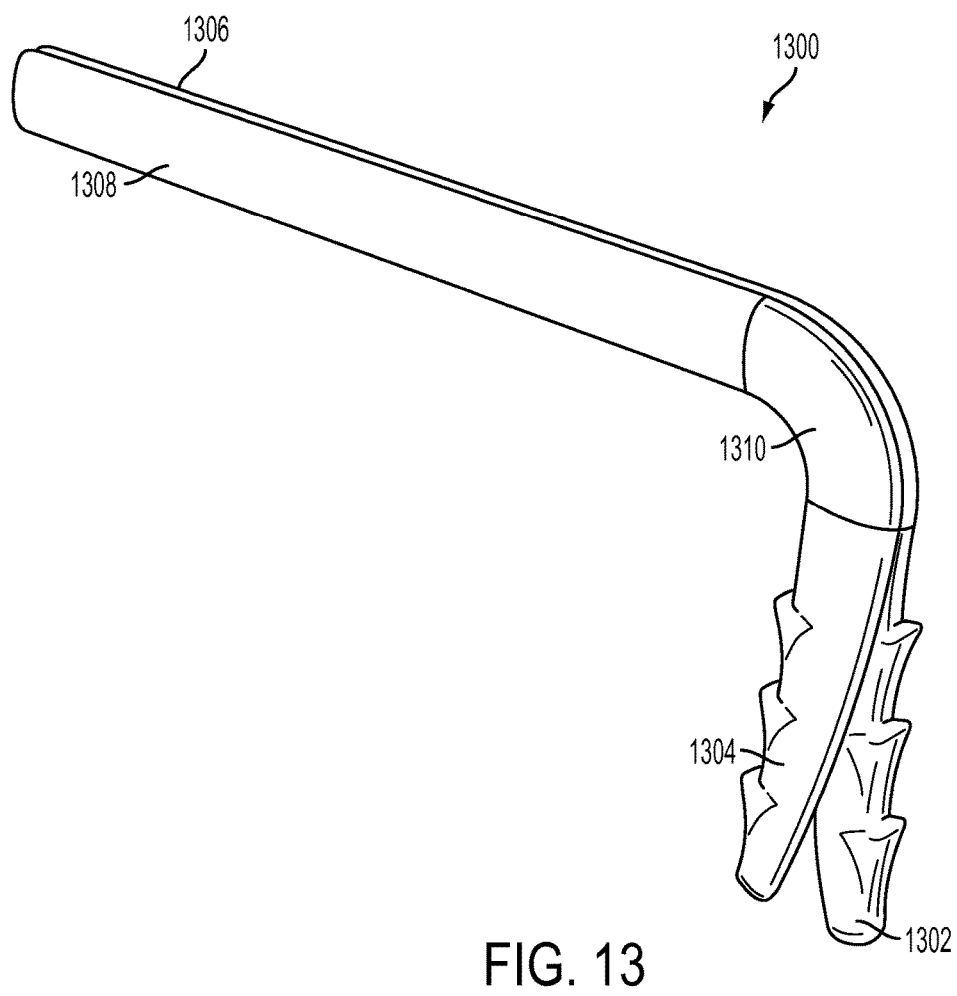
FIG. 13 is a perspective view of an embodiment of a bone anchor of the present invention wherein each probe component includes a rod section connected thereto that forms a spinal fixation element when aligned together.

FIG. 13 illustrates an exemplary bone anchor 1300 including first and second probe components 1302, 1304 that are connected at their proximal ends to first and second rod sections 1306, 1308. The connection can include a hinge portion 1310 in each rod section that allows the rod sections 1306, 1308 to rotate relative to the probe components 1302, 1304. This rotation can be used to connect the rod sections 1306, 1308 to additional bone anchors, or to collapse the bone anchor 1300, e.g., for easier introduction to a surgical site. Hinge portion 1310 can include any mechanical hinge known in the art. In some embodiments, hinge portion 1310 can be a "living" hinge integrated into the material of rod sections 1306, 1308. This can be accomplished, for example, by incorporating a different, more pliable material into the rod sections 1306, 1308 in the area of hinge portion 1310. Alternatively, hinge portion 1310 can be formed by simply using a thinner portion of material to allow bending. A notch or other deformation can also be included at hinge portion 1310 to promote bending in a particular location, as shown later in FIG. 22.

Figure 14:
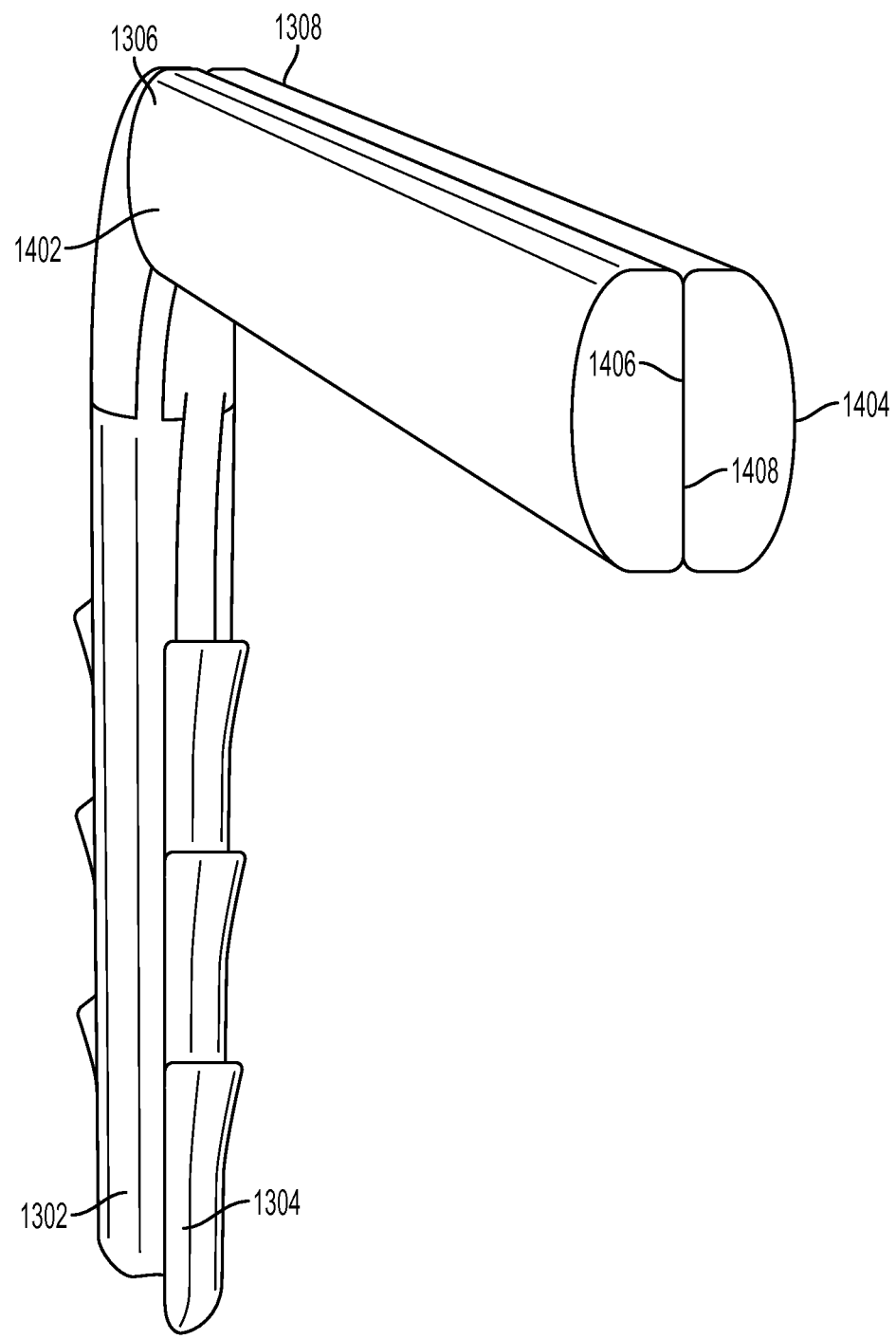
FIG. 14 is an alternate perspective view of the bone anchor in FIG. 13 showing the non-circular cross-sectional shape of the rod sections.

Referring to FIG. 14, an alternate view of bone anchor 1300 is shown illustrating the cross-sectional shape of the rod sections 1306, 1308. In some embodiments, the rod sections can form extensions of the probe components 1302, 1304. For example, in FIG. 14, each rod section 1306, 1308 includes an external face 1402, 1404 that can have a convex shape, similar to the external faces of probe components 1302, 1304, as discussed above. Rod sections 1306, 1308 can each further include an internal face 1406, 1408 that can be substantially linear, similar to the internal faces of the first and second probe components. However, in other embodiments, the rod sections, and even the probe components themselves, can have a variety of other cross-sectional shapes that complement each other and are configured to mate together. Any of these other cross-sectional shapes (e.g., half circles, interlocking ridges, diagonals, tongue and groove, etc.) are considered within the scope of the present invention.

Figure 15:
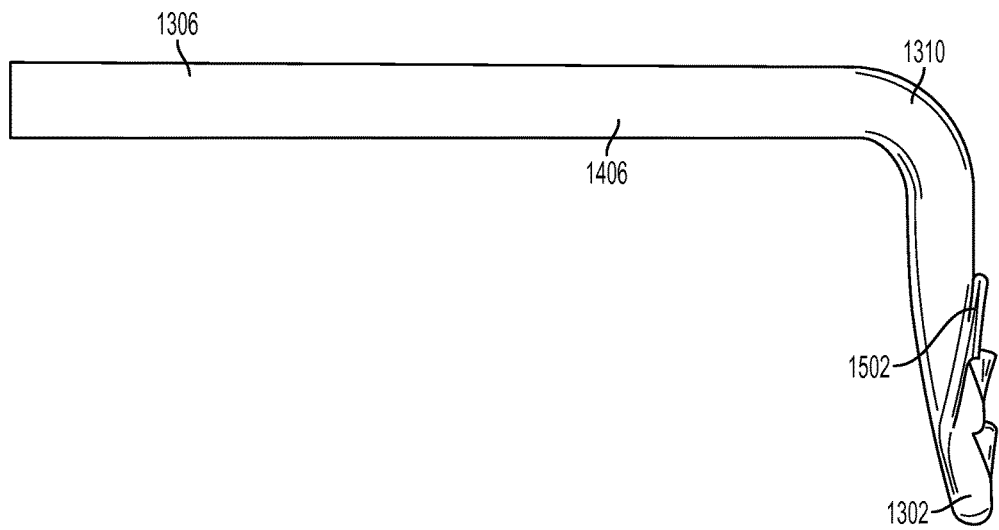
FIG. 15 is a perspective view of the internal surface of the first probe component of the bone anchor in FIG. 13.
Figure 16:
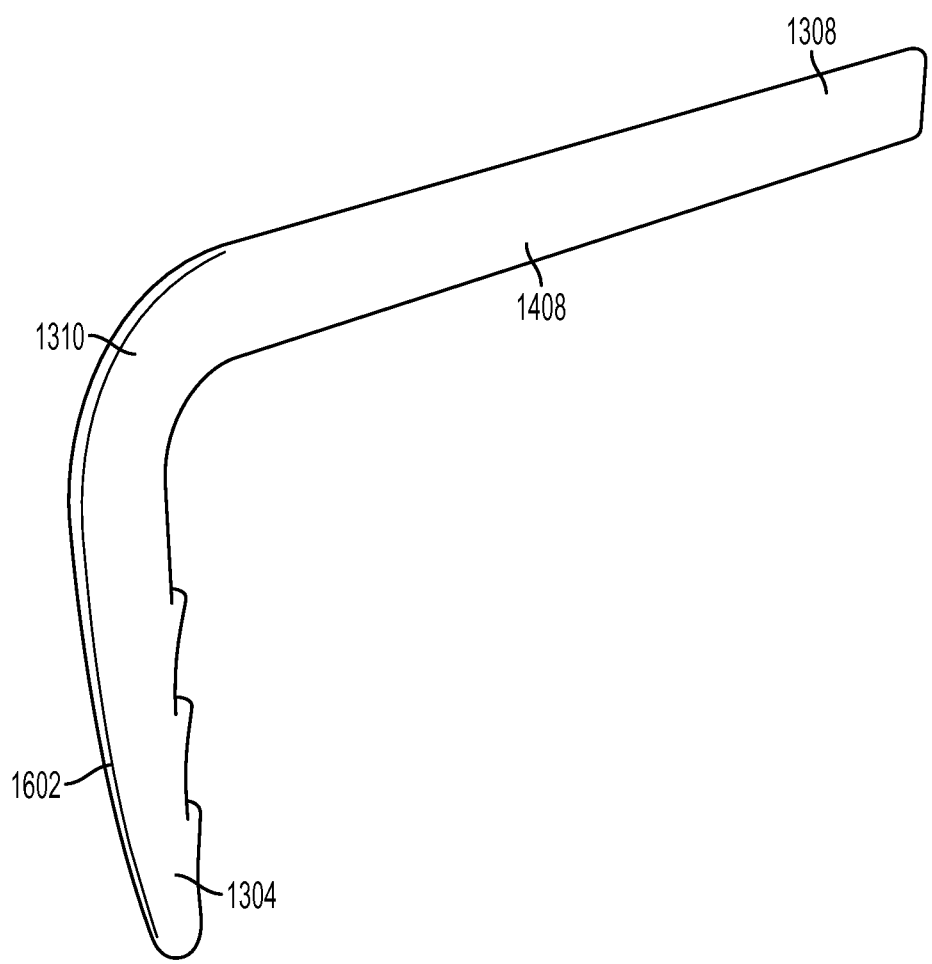
FIG. 16 is a perspective view of the internal surface of the second probe component of the bone anchor in FIG. 13.

FIGS. 15 and 16 illustrate the internal surfaces of exemplary probe components 1302, 1304 with connected rod sections 1306, 1308. With reference to FIG. 15 in particular, probe component 1302 is very similar to the first probe component 102 discussed above. The probe component 1302 includes an internal surface 1406 and a guide shoulder 1502 configured to interface with probe component 1304. Probe component 1304, illustrated in FIG. 16, includes an internal surface 1408 and a mating edge 1602 configured to interface with internal surface 1406 and guide shoulder 1502 of probe component 1302.

Figure 17:
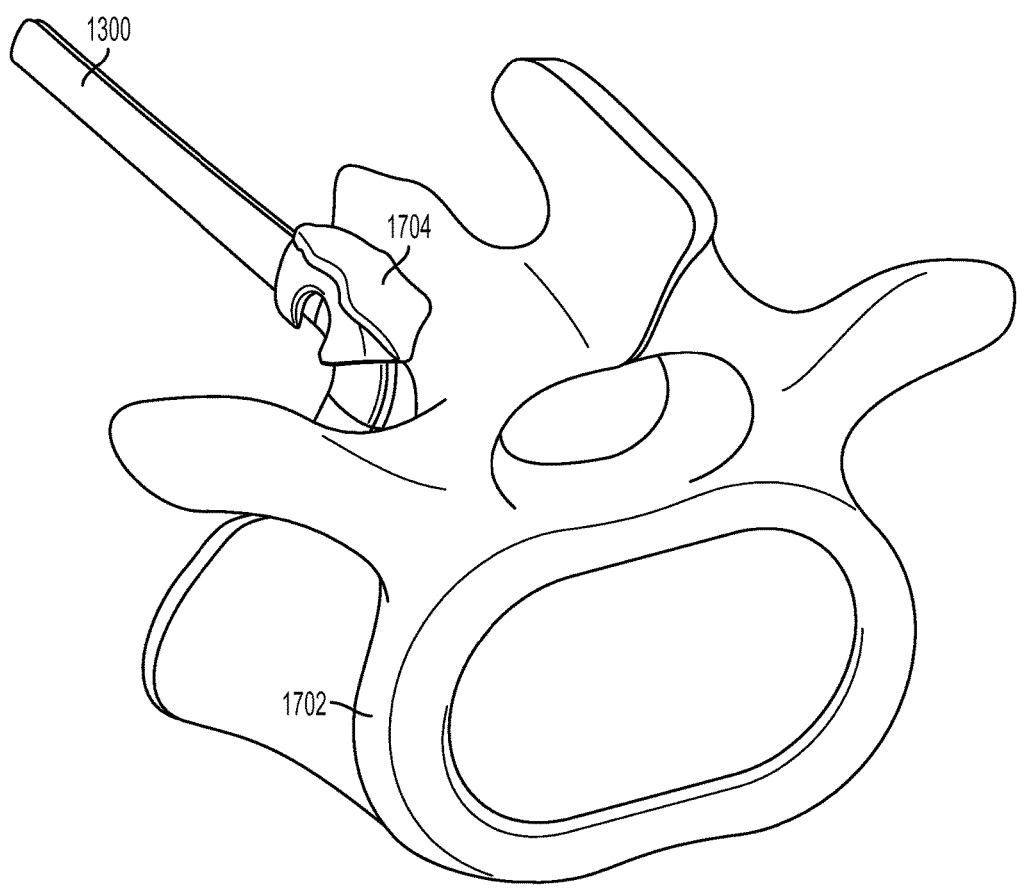
FIG. 17 is a perspective view of the bone anchor in FIG. 13 implanted in a vertebral body and including a crimp head to retain the proximal heads and rod sections of each probe component in relation to each other.
Figure 18:
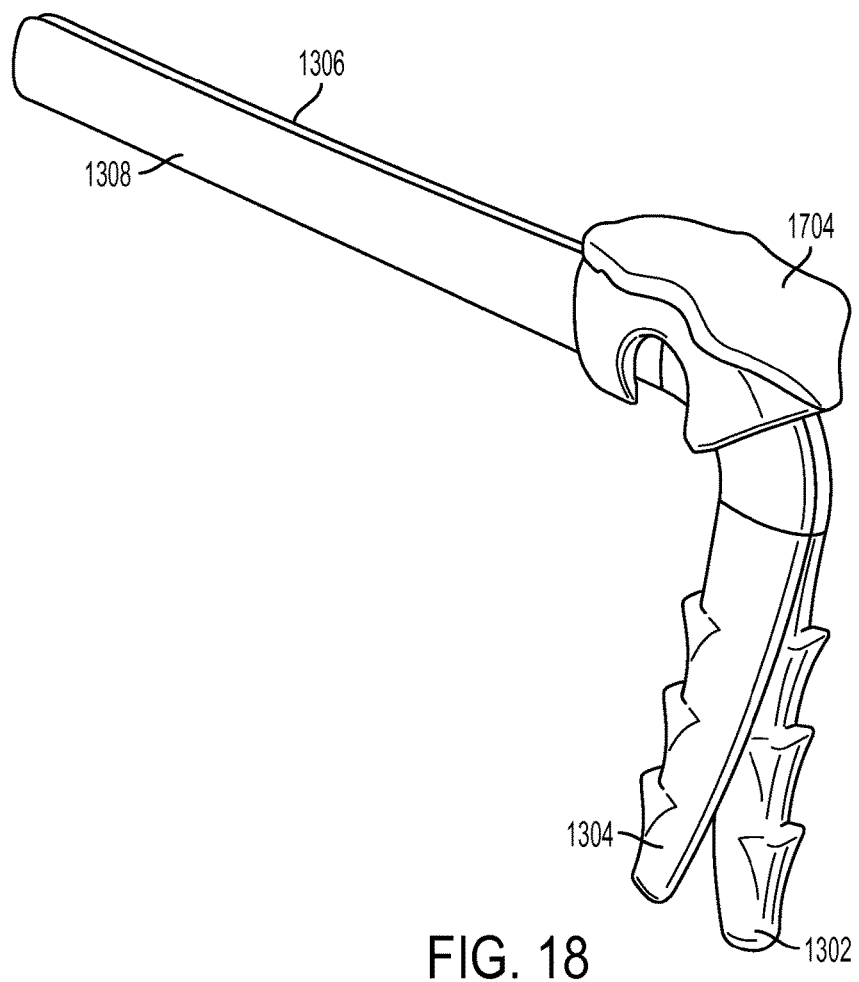
FIG. 18 is a perspective view of the bone anchor in FIG. 17 showing the crimp head retaining the proximal heads and rod sections of each probe component in relation to each other.

FIG. 17 illustrates an embodiment of bone anchor 1300 implanted in a vertebrae 1702. The probe components 1302, 1304 are implanted inside the vertebrae, and rod sections 1306, 1308 extend outside the vertebrae. Also shown is an exemplary embodiment of a crimp head 1704 that is configured to work with the bone anchor 1300. An alternate perspective view of bone anchor 1300 and crimp head 1704 is shown in FIG. 18 for clarity.

Figure 19:
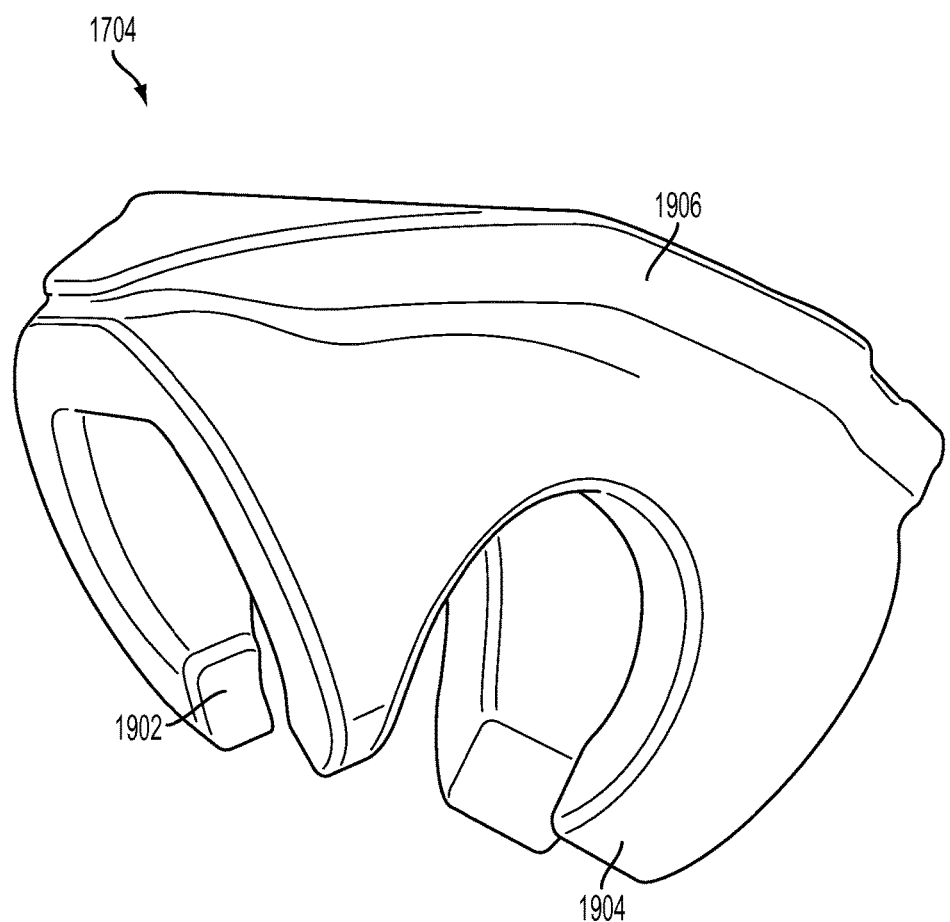
FIG. 19 is an alternate perspective view of the crimp head in FIG. 18.

Crimp head 1704 is shown in isolation in FIG. 19. Similar to the crimp head 300 discussed above, crimp head 1704 can include clamping arms 1902 to securely retain probe components 1302, 1304 in a fixed relationship with each other. Crimp head 1704, however, can also include an additional set of clamping arms 1904 configured to retain the rod sections 1306, 1308 in a fixed relationship with each other. The sets of clamping arms 1902, 1904 can be connected by a supporting portion 1906. Supporting portion 1906 can be configured to provide additional clamping force to the rod sections 1306, 1308. In addition, supporting portion 1906 can be configured to provide stress relief and support for the hinge portion 1310 after implantation.

Figure 20:
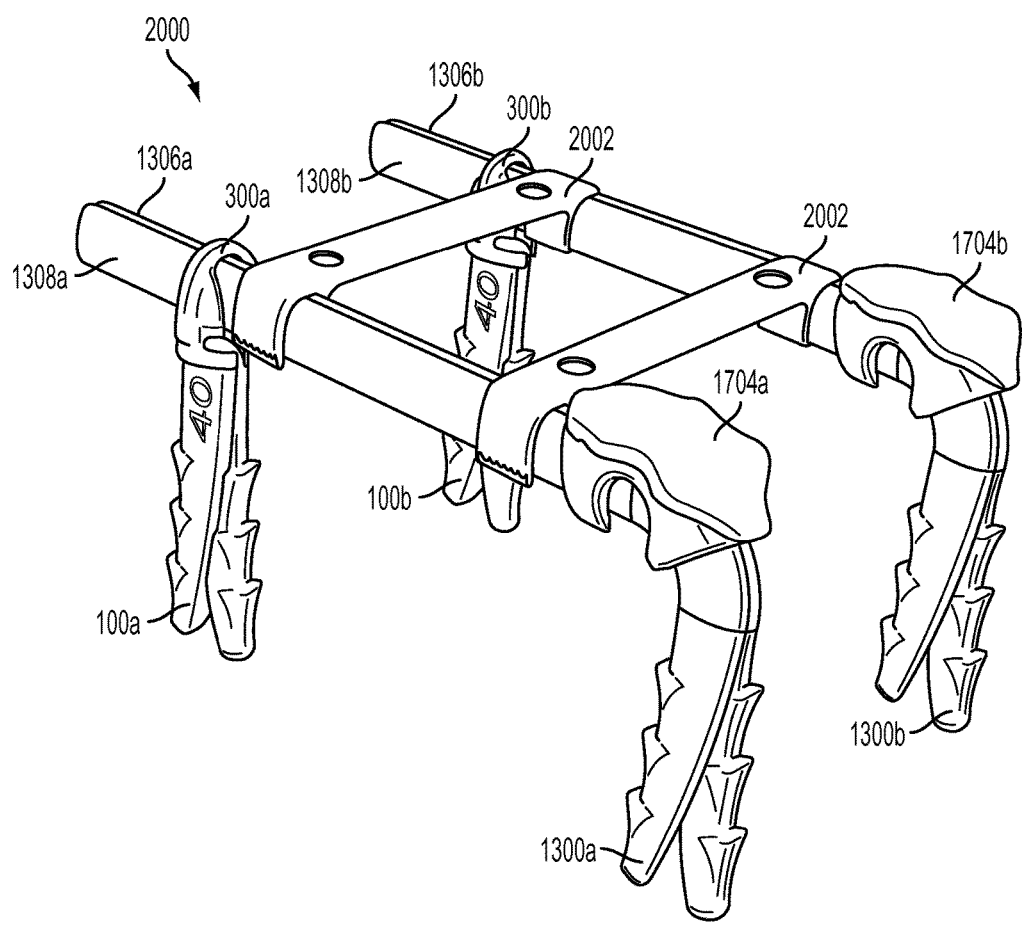
FIG. 20 is a perspective view of an embodiment of a spinal fixation assembly of the present invention including various embodiments of the bone anchors disclosed herein.

The various embodiments disclosed herein can be combined as modular components to create a complete spinal fixation assembly requiring fewer components and less complicated procedures to implant within a patient. An exemplary spinal fixation assembly 2000 is illustrated in FIG. 20. The assembly 2000 includes two bone anchors 1300a, 1300b having connected rod sections 1306a, 1308a, 1306b, 1308b. The anchors are secured by crimp heads 1704a and 1704b. The rod sections are connected to additional bone anchors 100a, 100b by being seated in the fixation element receiving seats 128a, 128b and secured by crimp heads 300a, 300b. The spinal fixation assembly 2000 can also serve as a foundation for attaching various other spinal fixation accessories, such as one or more transverse supporting members 2002. Crimp heads 1704 can also be provided in transversely connected pairs, incorporating the transverse supporting feature. Transverse supporting members 2002 can be formed from any biocompatible material and, in exemplary embodiments, are formed from titanium or a titanium alloy. Many additional modular combinations of the components disclosed herein are possible and all are considered within the scope of the present invention.

Figure 21:
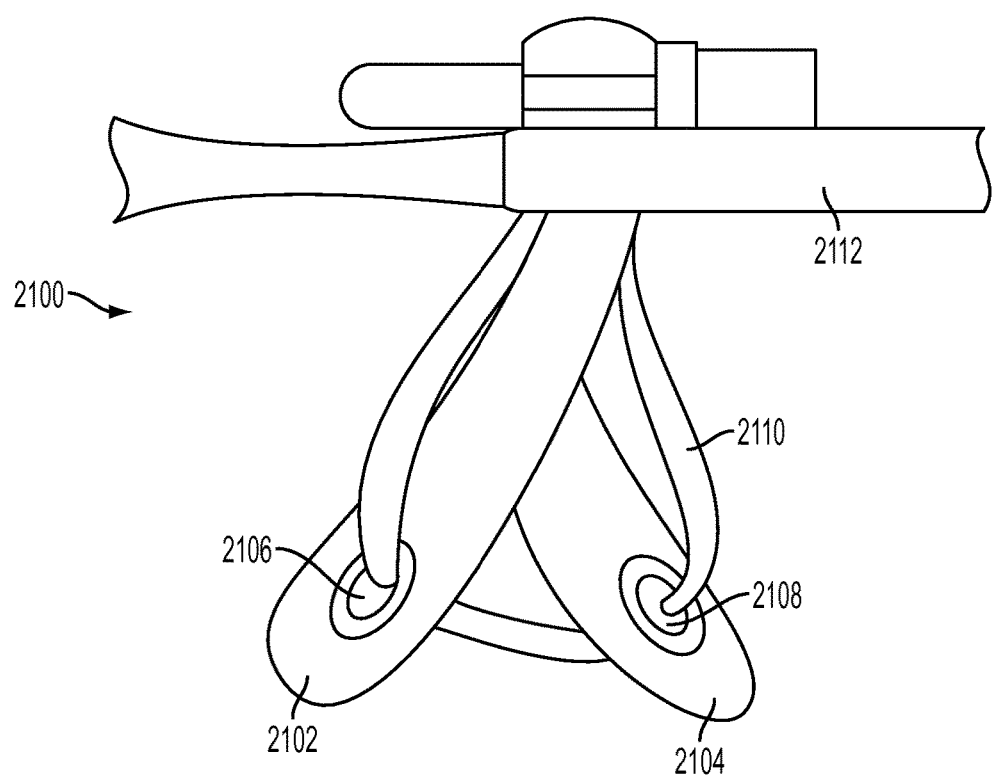
FIG. 21 is a cross-sectional view of an embodiment of a bone anchor of the present invention configured to function as a suture anchor.

In addition, the bone anchors of the present invention can be easily configured to provide anchoring in any application requiring securing a component or tissue to bone. For example, an exemplary bone anchor 2100 of the present invention is shown in FIG. 21 functioning as a suture anchor. Bone anchor 2100 includes first and second probe components 2102, 2104 similar to bone anchor 100 discussed above. First and second probe components 2102, 2104 each further include a suture receiving portion 2106, 2108, which can be a bore formed through the probe component and configured to receive a threaded suture 2110 therethrough. Suture 2110 can then extend out of the cavity formed in bone 2112 and be utilized to accomplish any of a variety of tasks. In the embodiment illustrated in FIG. 21, the proximal heads of probe components 2102, 2104 can be retained in a fixed relationship with each other by a ring clip 2114. Ring clip 2114 provides the same retaining function as the crimp heads and polyaxial receiving heads discussed above, but has a lower profile design that minimizes the protrusion of the bone anchor from the bone surface.

Figure 22:
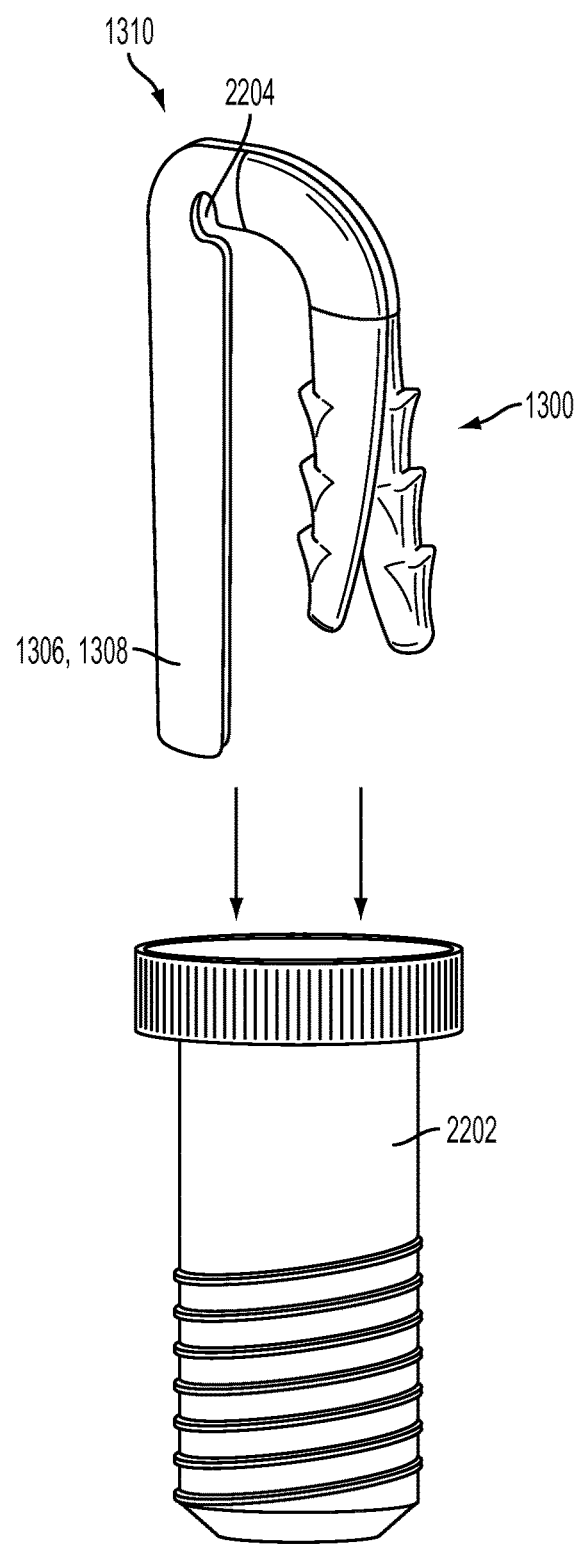
FIG. 22 is a front view of an embodiment of a bone anchor of the present invention including a rod section connected to each probe component and a hinge area that allows each probe component to be folded and introduced through, for example, a laparoscopic port.

The present invention also provides methods for using the bone anchors disclosed herein. Bone anchors of the present invention can be utilized in a variety of procedures, including open surgery and minimally invasive procedures. In minimally invasive procedures, each bone anchor component must be delivered to the surgical site through, for example, an appropriately sized and shaped port similar to the port 2202 illustrated in FIG. 22. In order to facilitate delivery through restricted spaces such as port 2202, bone anchor components of the present invention can include features to reduce their size or area footprint. Exemplary features include the hinge portion 1310 discussed above and illustrated in FIG. 22. Hinge portion 1310 of bone anchor 1300 in FIG. 22 utilizes a thinner portion of material and a pre-formed notch 2204 to allow the bone anchor to be collapsed as shown in the figure. Once at the surgical site, the rod sections 1306, 1308 can be rotated back into position to connect with other bone anchor components to form a spinal fixation assembly like that shown in FIG. 20. In addition, the probe components and attached rod sections can be delivered together, as shown in FIG. 22, or separately.

Figure 23:
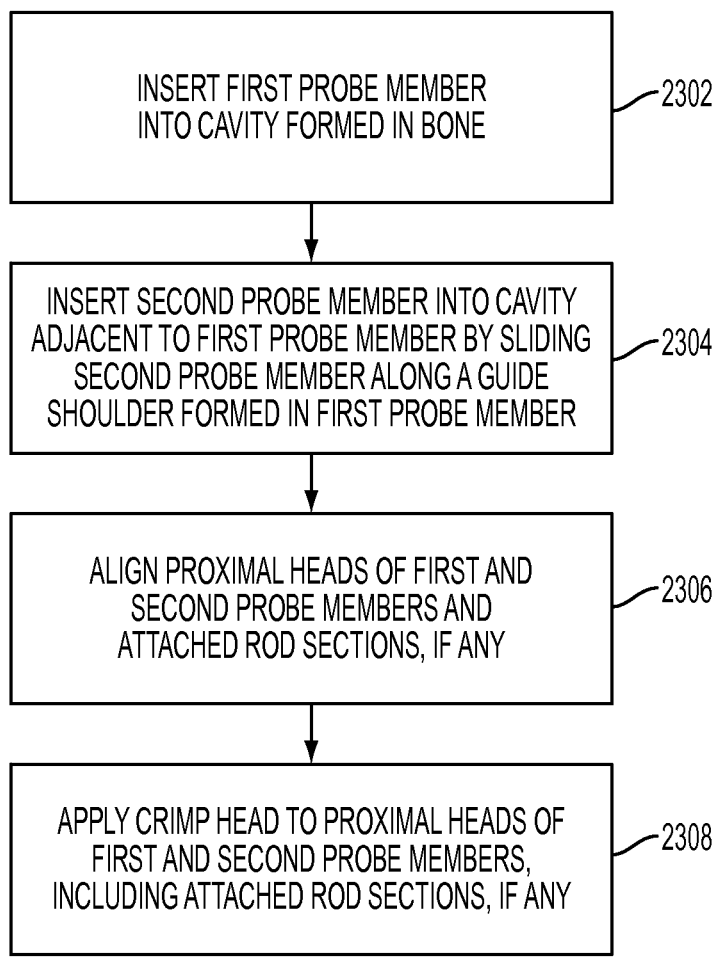
FIG. 23 is a flow diagram illustrating an embodiment of a method of the present invention.

Turning now to FIG. 23, a method of anchoring an implant to bone is provided that includes the step of inserting a first probe component or member into a cavity formed in bone [step 2302]. The probe member can be inserted straight into the cavity formed in bone, or along an arced path.

In the embodiments discussed above, inserting the first probe member 102 first can be important, because the guide shoulder 124 can direct the second probe member as it is inserted. In some other embodiments, however, the first probe member may not include a guide shoulder 124. In such embodiments, the divergence of the distal tips can be accomplished through the alignment and fixed relationship of the proximal heads of the probe members alone. In these embodiments, it does not matter whether the first probe member or the second probe member is inserted first.

Following insertion of the first probe member, a second probe component or member can be inserted into the cavity formed in the bone adjacent to the first probe member [step 2304]. This can be accomplished, for example, by sliding the second probe member along an internal surface of the first probe member such that a mating edge of the second probe member interfaces with a guide shoulder formed on the internal surface of the first probe member. The guide shoulder can cause the distal tip of the second probe member to diverge from the distal tip of the first probe member as the second probe member is inserted into the bone cavity.

Following insertion of both probe members, the proximal heads of the first and second probe members can be aligned [step 2306]. If the probe members include any connected rod sections, these can be aligned as well and rotated into position to connect with additional bone anchors. In addition, any other spinal fixation elements that need to be mated to the bone anchor can be seated, for example by seating the element in the fixation element receiving seat formed by the proximal heads of the first and second probe members.

Finally, a crimp head can be applied to the aligned proximal heads of the first and second probe members to retain them in a fixed relationship with each other [step 2308]. The crimp head can further retain any spinal fixation elements seated in, for example, the fixation element receiving seat of a bone anchor.

In embodiments that utilize an implant for fusing two vertebral bodies together, a polyaxial receiving head, or any other receiving head assembly having a closed lumen, steps 2302-2308 can be performed after positioning the implant, receiving head, or other receiving head assembly in position over a hole formed in the bone. Each probe member can then be inserted through both the implant, receiving head, or screw assembly, as well as the bone. Following insertion, and in place of step 2308 above, a set screw can be applied to retain the proximal ends of the probe members in a fixed relationship with each other and to retain a spinal fixation element to the bone anchor.

Bone anchors of the present invention provide an additional benefit over prior art anchors in that they are easily removable following spinal fixation and natural healing. To remove the bone anchors, the steps of the method illustrated in FIG. 23 are simply reversed. For example, any crimp head, polyaxial bone screw, implant set screw, or other accessory can be removed to free the first and second probe members from one another. The second probe member can then be removed from the cavity formed in the bone by rotating the second probe member such that its distal tip converges with the distal tip of the first probe member. This movement will disengage the bone engaging edge of the second probe member, thereby allowing its removal from the cavity. The first probe member can then be similarly repositioned to disengage its bone engaging edge and subsequently removed from the cavity.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

The invention claimed is:

1. An intervertebral implant, comprising:
   an implant body having opposed bone-engaging surfaces and at least one sidewall extending between the bone-engaging surfaces, wherein the implant body includes at least one lumen formed therein that extends from one of the opposed bone-engaging surfaces to the at least one sidewall;
   at least one bone anchor that includes a first probe component and a separate second probe component, wherein each of the first and second probe components are configured to be independently inserted into the at least one lumen from the at least one sidewall such that a distal end of each probe component protrudes from one of the opposed bone-engaging surfaces; and
   a set screw configured to be received within a threaded lumen formed in the at least one sidewall such that the set screw, in combination with a sidewall of the at least one lumen, retains proximal heads of the first and second probe components of the at least one bone anchor in a fixed relationship with each other;
   wherein each of the at least one lumens is configured to receive both the first probe component and the second probe component of a bone anchor; and
   wherein each of the first probe component and the second probe component of the at least one bone anchor includes a bone-engaging portion and a portion that contacts the other probe component when disposed in the at least one lumen.

2. The implant of claim 1, wherein the implant body includes a first lumen and a second lumen formed therein, along with a first bone anchor and a second bone anchor.

3. The implant of claim 1, wherein the implant body includes an inner void configured to be filled with a biologic agent or other bone growth promoting material.

4. The implant of claim 3, wherein the at least one sidewall includes one or more openings in communication with the inner void of the implant body.

5. The implant of claim 1, wherein each of the opposed bone-engaging surfaces are textured.

6. The implant of claim 1, wherein the first and second probe components of the at least one bone anchor have flat proximal ends configured to abut against an interface portion of the set screw when the at least one bone anchor is inserted into the at least one lumen of the implant body and the set screw is received within the threaded lumen formed in the at least one sidewall.

7. The implant of claim 1, wherein the first and second probe components are curved.

8. The implant of claim 1, wherein:
the first probe component of the at least one bone anchor includes a bone-engaging edge having a plurality of barbs, an opposed edge, an external surface, and an opposed internal surface having a guide shoulder formed thereon, the guide shoulder extending in a diagonal curve across the internal surface of the first probe component; and
the second probe component of the at least one bone anchor includes a bone-engaging edge having a plurality of barbs, a mating edge having a profile complementary to the guide shoulder and being configured to be seated along the guide shoulder, an external surface, and an opposed internal surface.

9. The implant of claim 8, wherein the first and second probe components of the at least one bone anchor are configured to be assembled such that the barbed bone-engaging edges of the first probe component and the second probe component face away from one another, the external surfaces of the first probe component and the second probe component face away from one another, and the mating edge of the second probe component is seated along the guide shoulder of the first probe component.

10. The implant of claim 9, wherein a distal tip of each probe component of the at least one bone anchor diverges away from a central longitudinal axis of the at least one bone anchor such that a distance between the first probe component and the second probe component increases from a proximal end of the bone anchor to a distal end of the bone anchor.

11. The implant of claim 8, wherein the internal surfaces of the first probe component and the second probe component of the at least one bone anchor are substantially planar.

12. The implant of claim 8, wherein the external surfaces of the first and second probe components of the at least one bone anchor are convex.

13. The implant of claim 1, wherein the first probe component and the second probe component of the at least one bone anchor are formed from any of titanium, a titanium alloy, polyether ether ketone (PEEK), and reinforced PEEK.

14. The implant of claim 1, wherein the first probe component and the second probe component of the at least one bone anchor are formed from a radiolucent material.

15. An intervertebral implant, comprising:
an implant body having opposed bone-engaging surfaces and at least one sidewall extending between the bone-engaging surfaces, wherein the implant body includes at least at least one lumen formed therein that extends from one of the opposed bone-engaging surfaces to the at least one sidewall;
at least one bone anchor that includes a first probe component and a second probe component, wherein each of the first and second probe components are configured to be inserted into the at least one lumen from the at least one sidewall such that a distal end of each probe component protrudes from one of the opposed bone-engaging surfaces; and
a set screw configured to be received within a threaded lumen formed in the at least one sidewall such that the set screw, in combination with a sidewall of the at least one lumen, retains proximal heads of the first and second probe components of the at least one bone anchor in a fixed relationship with each other;
wherein the first probe component of the at least one bone anchor includes a bone-engaging edge having a plurality of barbs, an opposed edge, an external surface, and an opposed internal surface having a guide shoulder formed thereon, the guide shoulder extending in a diagonal curve across the internal surface of the first probe component; and
wherein the second probe component of the at least one bone anchor includes a bone-engaging edge having a plurality of barbs, a mating edge having a profile complementary to the guide shoulder and being configured to be seated along the guide shoulder, an external surface, and an opposed internal surface.

16. The implant of claim 15, wherein the first and second probe components of the at least one bone anchor are configured to be assembled such that the barbed bone-engaging edges of the first probe component and the second probe component face away from one another, the external surfaces of the first probe component and the second probe component face away from one another, and the mating edge of the second probe component is seated along the guide shoulder of the first probe component.

17. The implant of claim 16, wherein a distal tip of each probe component of the at least one bone anchor diverges away from a central longitudinal axis of the at least one bone anchor such that a distance between the first probe component and the second probe component increases from a proximal end of the bone anchor to a distal end of the bone anchor.

18. The implant of claim 15, wherein the internal surfaces of the first probe component and the second probe component of the at least one bone anchor are substantially planar.

19. The implant of claim 15, wherein the external surfaces of the first and second probe components of the at least one bone anchor are convex.

20. An intervertebral implant, comprising:
an implant body having opposed bone-engaging surfaces and a sidewall extending between the bone-engaging surfaces, wherein the implant body includes a first lumen formed therein that extends from one of the opposed bone-engaging surfaces to the sidewall;
a bone anchor that includes a first probe component and a separate second probe component, wherein each of the first and second probe components are configured to be independently inserted into the first lumen from the sidewall such that a distal end of each probe component protrudes from one of the opposed bone-engaging surfaces; and
a set screw configured to be received within a threaded second lumen formed in the sidewall such that the set screw, in combination with a sidewall of the first lumen, retains proximal heads of the first and second probe components of the bone anchor in a fixed relationship with each other;

wherein each of the first probe component and the second probe component contacts the sidewall of the first lumen when disposed in the first lumen.

\* \* \* \* \*